United States Patent
Utsunomiya et al.

(10) Patent No.: US 10,806,407 B2
(45) Date of Patent: Oct. 20, 2020

(54) MEDICAL INFORMATION PROCESSING SYSTEM

(71) Applicant: CANON MEDICAL SYSTEMS CORPORATION, Otawara-shi (JP)

(72) Inventors: Kazuki Utsunomiya, Nasushiobara (JP); Yusuke Kano, Nasushiobara (JP); Kazumasa Noro, Takanezawa (JP); Longxun Piao, Nasushiobara (JP)

(73) Assignee: CANON MEDICAL SYSTEMS CORPORATION, Otawara-shi (JP)

( * ) Notice: Subject to any disclaimer, the term of this patent is extended or adjusted under 35 U.S.C. 154(b) by 0 days.

(21) Appl. No.: 16/044,750

(22) Filed: Jul. 25, 2018

(65) Prior Publication Data

US 2019/0029610 A1 Jan. 31, 2019

(30) Foreign Application Priority Data

Jul. 28, 2017 (JP) ................. 2017-147101

(51) Int. Cl.

| A61B 5/00 | (2006.01) |
|---|---|
| A61B 5/01 | (2006.01) |
| G16H 40/63 | (2018.01) |
| A61B 5/0205 | (2006.01) |
| G16H 10/60 | (2018.01) |
| G16H 50/70 | (2018.01) |
| A61B 5/1455 | (2006.01) |
| A61B 5/021 | (2006.01) |

(52) U.S. Cl.
CPC .............. *A61B 5/7425* (2013.01); *A61B 5/01* (2013.01); *A61B 5/0205* (2013.01); *A61B 5/02055* (2013.01); *A61B 5/742* (2013.01); *A61B 5/743* (2013.01); *A61B 5/7435* (2013.01); *G16H 10/60* (2018.01); *G16H 40/63* (2018.01); *G16H 50/70* (2018.01); *A61B 5/021* (2013.01); *A61B 5/14551* (2013.01)

(58) Field of Classification Search
CPC ....... A61B 5/7425; A61B 5/01; A61B 5/0205; A61B 5/743; A61B 5/021; A61B 5/014551; G16H 40/63
USPC ...................................... 340/815.4
See application file for complete search history.

(56) References Cited

U.S. PATENT DOCUMENTS

| 10,248,762 B2* | 4/2019 | Treacy ............. G16H 10/60 |
|---|---|---|
| 2003/0117296 A1* | 6/2003 | Seely .............. A61B 5/0002 340/870.07 |
| 2005/0055243 A1* | 3/2005 | Arndt ............ G06F 19/3418 705/2 |
| 2007/0176931 A1* | 8/2007 | Tivig .............. G16H 40/63 345/440 |

(Continued)

FOREIGN PATENT DOCUMENTS

JP 2014-179091 9/2014

*Primary Examiner* — Emily C Terrell
(74) *Attorney, Agent, or Firm* — Oblon, McClelland, Maier & Neustadt, L.L.P.

(57) ABSTRACT

A medical information processing system comprises processing circuitry configured to acquire numerical data representing medical information together with date and time information associated with the numerical data, display the numerical data in time series based on the date and time information, specify a period relating to the numerical data displayed in time series, calculate a distribution of the numerical data contained in the period, and further display the distribution graphically.

20 Claims, 20 Drawing Sheets

(56) References Cited

U.S. PATENT DOCUMENTS

| | | | |
|---|---|---|---|
| 2013/0047113 A1* | 2/2013 | Hume | G06Q 50/22 |
| | | | 715/771 |
| 2014/0218368 A1* | 8/2014 | Hatano | G06F 3/147 |
| | | | 345/440 |
| 2014/0275819 A1 | 9/2014 | Kassem et al. | |
| 2017/0340294 A1 | 11/2017 | Kassem et al. | |
| 2020/0043606 A1* | 2/2020 | Segman | G16H 40/63 |

\* cited by examiner

FIG.2

| PATIENT ID | TYPE | MEASUREMENT DATE AND TIME | MEASURED VALUE |
|---|---|---|---|
| P1 | PULSE RATE | 06/07/2017 09:15 | 68 |
| P1 | BLOOD PRESSURE | 06/07/2017 09:15 | 141/89 |
| P1 | BODY TEMPERATURE | 06/07/2017 09:15 | 36.5 |
| P2 | PULSE RATE | 06/14/2017 14:45 | 59 |
| P2 | BLOOD PRESSURE | 06/14/2017 14:45 | 131/81 |
| ... | ... | ... | ... |

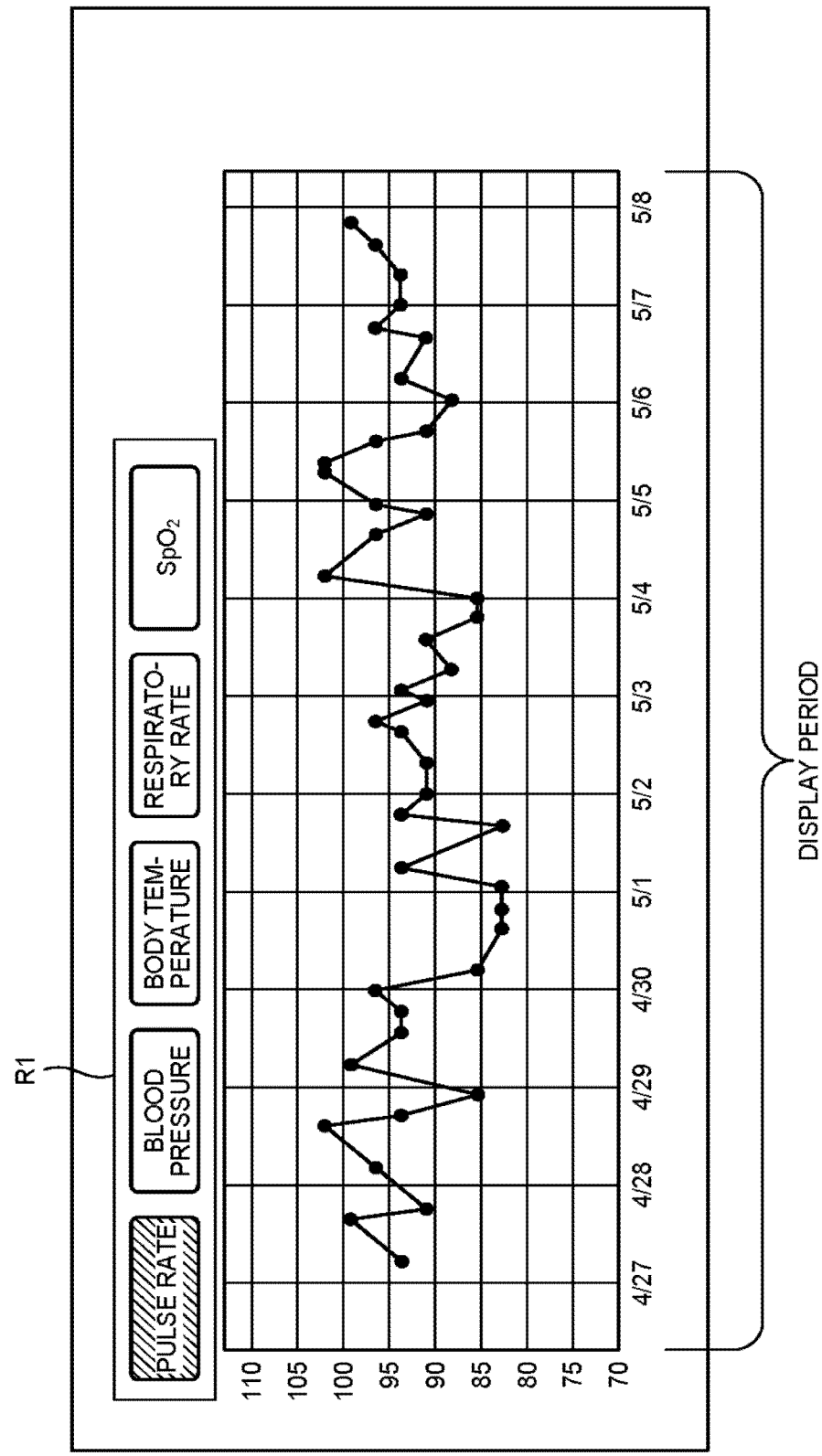

FIG.3B

| TIME | DISPLAY MEANING |
|---|---|
| 4/27/2017 00:00:00 | START TIME |
| 5/08/2017 00:00:00 | END TIME |

FIG.4A

| PATIENT ID | TYPE | MEASUREMENT DATE AND TIME | MEASURED VALUE |
|---|---|---|---|
| P1 | PULSE RATE | 04/26/2017 09:15 | 65 |
| P1 | PULSE RATE | 04/26/2017 15:30 | 68 |
| P1 | PULSE RATE | 04/26/2017 20:00 | 65 |
| P1 | PULSE RATE | 04/27/2017 09:00 | 54 |
| P1 | PULSE RATE | 04/27/2017 14:45 | 53 |
| P1 | PULSE RATE | 04/27/2017 21:30 | 75 |
| P1 | PULSE RATE | 04/28/2017 09:00 | 61 |
|  |  |  |  |
| P1 | PULSE RATE | 05/06/2017 14:45 | 68 |
| P1 | PULSE RATE | 05/06/2017 21:30 | 71 |
| P1 | PULSE RATE | 05/07/2017 09:00 | 67 |
| P1 | PULSE RATE | 05/07/2017 14:45 | 70 |
| P1 | PULSE RATE | 05/07/2017 21:30 | 55 |
| P1 | PULSE RATE | 05/08/2017 09:30 | 72 |
| P1 | PULSE RATE | 05/08/2017 12:30 | 60 |
| ... | ... | ... | ... |

DISPLAY PERIOD

FIG.4B

| DATA INTERVAL | FREQUENCY |
|---|---|
| TO 50 | 0 |
| TO 55 | 3 |
| TO 60 | 0 |
| TO 65 | 1 |
| TO 70 | 3 |
| TO 75 | 2 |

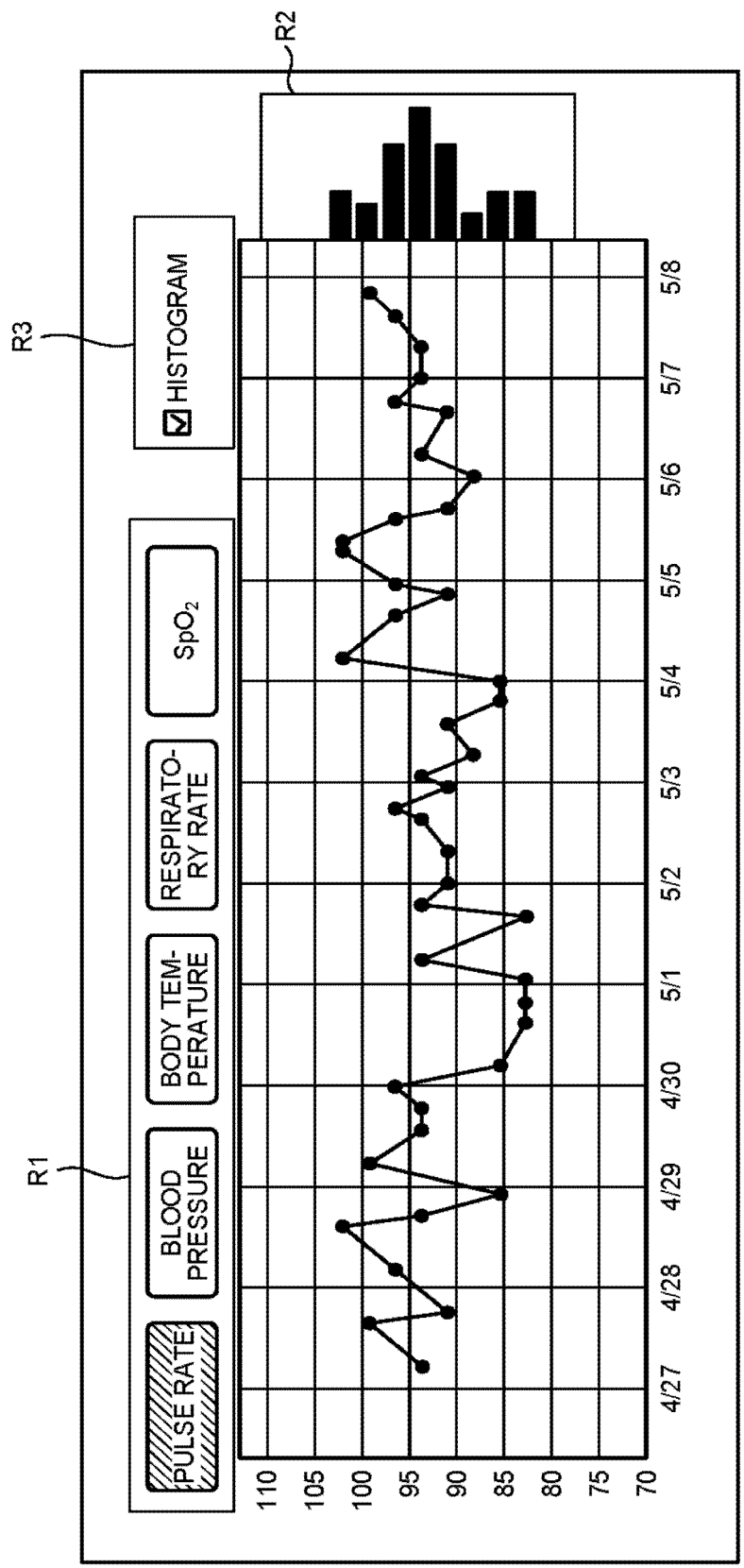

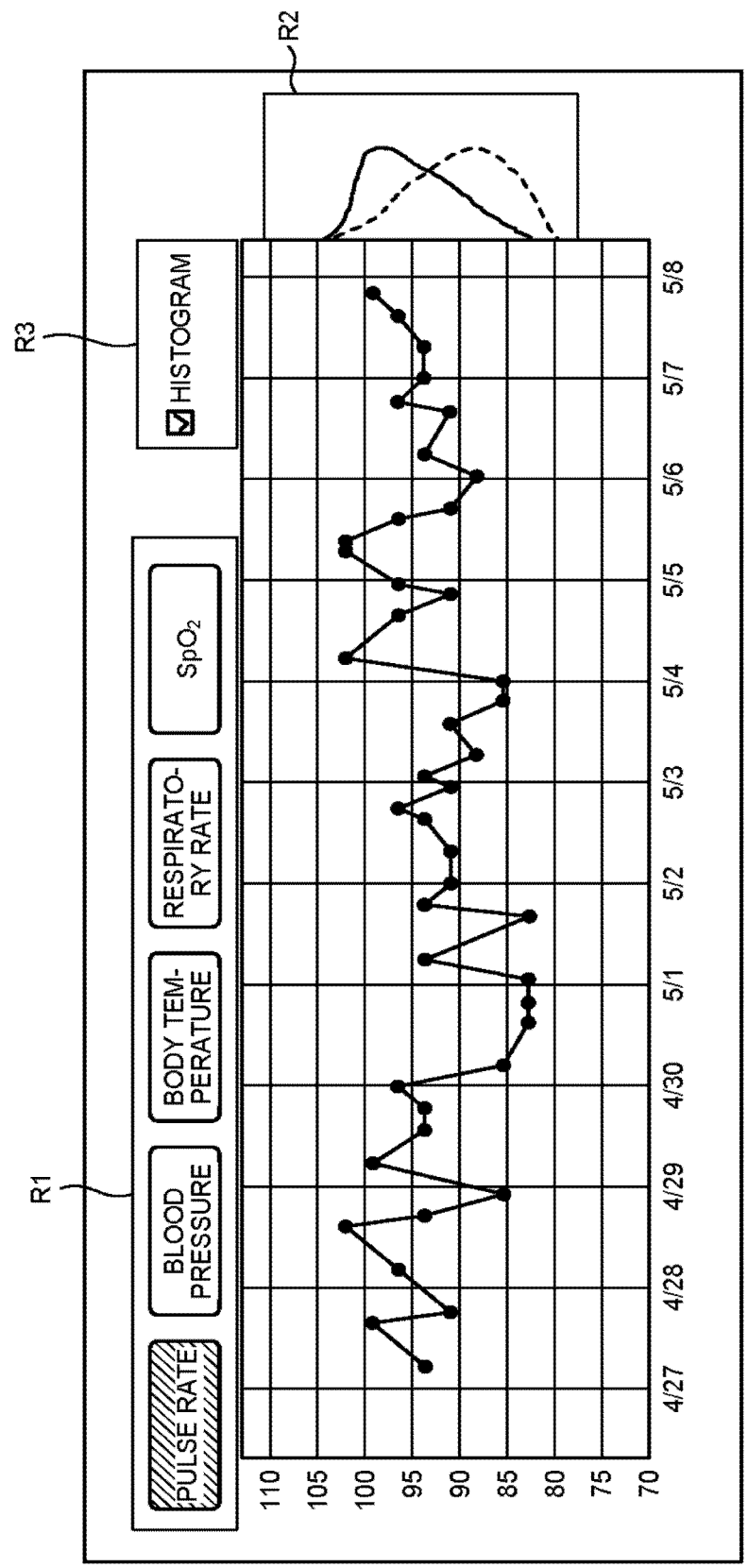

FIG.8A

| AVERAGE | 63.77778 |
|---|---|
| STANDARD ERROR | 2.742554 |
| MEDIAN | 67 |
| STANDARD DEVIATION | 8.227663 |
| VARIANCE | 67.69444 |
| KURTOSIS | -1.69938 |
| SKEWNESS | -0.21493 |
| RANGE | 22 |
| MINIMUM | 53 |
| MAXIMUM | 75 |
| SUM | 574 |
| NUMBER OF SAMPLES | 9 |

| X COORDINATE | OPERATION CONTENT |
|---|---|
| 1.874 | START DRAG |
| 5.223 | DROP |

| TIME | DISPLAY MEANING |
|---|---|
| 4/28/2017 06:24:15 | START TIME |
| 5/1/2017 22:15:33 | END TIME |

US 10,806,407 B2

MEDICAL INFORMATION PROCESSING SYSTEM

CROSS-REFERENCE TO RELATED APPLICATIONS

This application is based upon and claims the benefit of priority from Japanese Patent Application No. 2017-147101, filed on Jul. 28, 2017; the entire contents of which are incorporated herein by reference.

FIELD

Embodiments described herein relate generally to a medical information processing system.

BACKGROUND

Doctors make diagnoses and provide treatments comprehensively using various types of data including image data about patients, numerical data that is acquired from the patients (body temperature, blood pressure, etc.), and numerical data that is acquired from the image data (diameter of blood vessel, blood flow, etc.). For example, when treating a heart failure, a doctor understands a data tendency of vital data (pulse rate, heart rate, etc.,) that is acquired in time series from a patient, thereby making a diagnosis and provides a treatment. Specifically, the doctor performs, in his/her head, a statistical process on each set of vital data that is acquired in time series, thereby understanding the content of current medication and the condition of heart failure and further adjusting the type of drug and dosage.

A method of plotting vital data in association with a time axis and displaying the vital data in time series is known; however, even if the vital data is displayed according to such a method, it is necessary to perform the statistical process in the doctor's head based on the display in order to understand the tendency of the vital data and thus it is difficult for doctors or nurses to understand data tendency immediately.

BRIEF DESCRIPTION OF THE DRAWINGS

FIG. 2 is a diagram representing exemplary vital data according to the first embodiment;

FIG. 3A is a diagram illustrating exemplary displaying vital data in time series according to the first embodiment;

FIG. 3B is a diagram for explaining a display period according to the first embodiment;

FIG. 4A is a diagram for explaining calculation of statistical information according to the first embodiment;

FIG. 4B is a diagram for explaining the calculation of statistical information according to the first embodiment;

FIG. 5 is a diagram illustrating exemplary display of statistical information according to the first embodiment;

FIG. 7 is a diagram illustrating exemplary display of statistical information according to the first embodiment;

FIG. 8A is a diagram for explaining calculation of statistical information according to the first embodiment;

DETAILED DESCRIPTION

A medical information processing system comprises processing circuitry. The processing circuitry is configured to acquire numerical data representing medical information together with date and time information associated with the numerical data. The processing circuitry is configured to display the numerical data in time series based on the date and time information. The processing circuitry is configured to specify a period relating to the numerical data displayed in time series. The processing circuitry is configured to calculate a distribution of the numerical data contained in the period. And the processing circuitry is further configured to display the distribution graphically.

With reference to the accompanying drawings, embodiments of the medical information processing system will be described in detail below.

Figure 1:
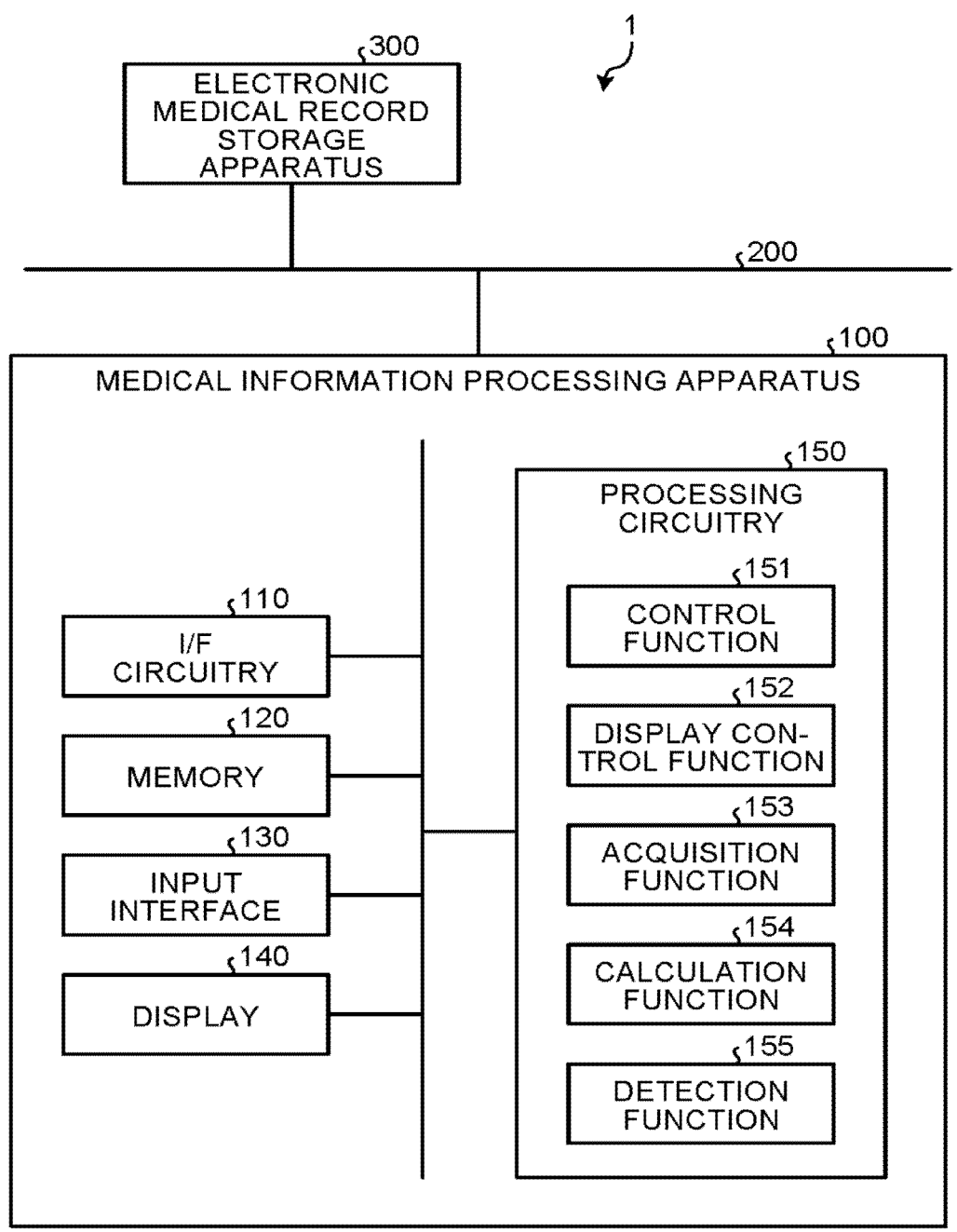
FIG. 1 is a block diagram illustrating an exemplary configuration of a medical information processing system according to a first embodiment.

FIG. 1 is a block diagram illustrating an exemplary configuration of a medical information processing system 1 according to a first embodiment. As illustrated in FIG. 1, the medical information processing system 1 includes a medical information processing apparatus 100, a network 200 and an electronic medical record storage apparatus 300.

As illustrated in FIG. 1, the medical information processing apparatus 100 is connected to the electronic medical record storage apparatus 300 via the network 200 such that they can communicate with each other. For example, the medical information processing apparatus 100 and the electronic medical record storage apparatus 300 are set in a hospital, or the like, and are connected with each other via the network 200, such as an internal LAN.

The electronic medical record storage apparatus 300 is an apparatus that stores medical data about various types of diagnosis and treatment that are made and provided in a hospital, or the like. For example, the electronic medical record storage apparatus 300 stores data (vital data), such as a pulse rate, a heart rate, a respiratory rate, a heart rate, a respiratory rate, a blood pressure, a body temperature and SpO$_2$ in association with date and time information. In an example, the electronic medical record storage apparatus 300 stores vital data in association with a time at which the measurement is performed and a time at which the vital data is input.

For example, the electronic medical record storage apparatus 300 is set as part of an electronic medical record system that is introduced to a hospital, or the like, and stores vital data that is generated by the electronic medical record system. For example, the electronic medical record storage apparatus 300 is realized by a computer device, such as a database (DB) server, and stores the vital data in a semiconductor memory device, such as a random access memory (RAM) or a flash memory, or a storage circuit, such as a hard disk or an optical disk.

The medical information processing apparatus 100 acquires vital data from the electronic medical record storage apparatus 300 via the network 200 and performs various types of information processing using the acquired vital data. For example, the medical information processing apparatus 100 is realized by a computer device, such as a work station.

Specifically, the medical information processing apparatus 100 includes interface (I/F) circuitry 110, a memory 120, an input interface 130, a display 140 and processing circuitry 150.

The I/F circuitry 110 is connected to the processing circuitry 150 and controls transmission and communication of various types of data to and with the electronic medical record storage apparatus 300. For example, the I/F circuitry 110 receives vital data from the electronic medical record storage apparatus 300 and outputs the received vital data to the processing circuitry 150. For example, the I/F circuitry 110 is realized by a network card, a network adapter, a network interface controller (NIC), or the like.

The memory 120 is connected to the processing circuitry 150 and stores various types of data. For example, the memory 120 stores the vital data that is received from the electronic medical record storage apparatus 300. For example, the memory 120 is realized by a semiconductor memory device, such as a random access memory (RAM) or a flash memory, a hard disk, an optical disk, or the like.

The input interface 130 is connected to the processing circuitry 150, converts an input operation that is received from an operator into electronic signals and outputs the electronic signals to the processing circuitry 150. For example, the input interface 130 is realized by a trackball, a switch button, a mouse, a keyboard, a touch panel, or the like.

The display 140 is connected to the processing circuitry 150 and displays various types of data that are output from the processing circuitry 150. For example, the display 140 is realized by a liquid crystal monitor, a cathode ray tube (CRT) monitor, a touch panel, or the like. The input interface 130 and the display 140 may be integrated. For example, the input interface 130 and the display 140 are realized by a touch panel.

The processing circuitry 150 controls the entire processes performed by the medical information processing apparatus 100 by executing a control function 151, a display control function 152, an acquisition function 153, a calculation function 154 and a detection function 155. For example, the processing circuitry 150 is realized by a processor.

For example, by loading a program corresponding to the control function 151 from the memory 120 and executing the program, the processing circuitry 150 causes the vital data that is output from the I/F circuitry 110 to be stored in the memory 120. For example, by loading a program corresponding to the display control function 152 and executing the program, the processing circuitry 150 reads the vital data stored in the memory 120 and displays the vital data on the display 140. For example, by loading a program corresponding to the display control function 152, the acquisition function 153, the calculation function 154 and the detection function 155 from the memory 120 and executing the program, the processing circuitry 150 calculates statistical information from the vital data and displays the statistical information on the display 140. Calculation and display of statistical information will be described below.

The entire configuration of the medical information processing system 1 according to the first embodiment has been described above. Having such a configuration, the medical information processing system 1 makes it easy to understand a tendency of data that is acquired in time series from a patient, such as vital data. Specifically, by performing the process performed by the processing circuitry 150 to be described in detail below, the medical information processing system 1 dynamically calculates statistical information from the vital data and displays the statistical information on the display 140, thereby making it easy to understand the data tendency. The processes performed by the medical information processing system 1 according to the first embodiment will be described in detail below.

First of all, the electronic medical record storage apparatus 300 stores vital data in association with date and time information. For example, the electronic medical record storage apparatus 300 stores vital data that is obtained by performing measurement on a patient and that is input by a doctor, nurse, or the like, who performs the measurement. When a time at which the measurement is performed is input together with the vital data, the electronic medical record storage apparatus 300 is able to store the vital data in association with the time at which the measurement is performed. The electronic medical record storage apparatus 300 is also able to store the vital data in association with the time at which the vital data is input.

In another example, the electronic medical record storage apparatus 300 stores the vital data that is acquired from a vital data measurement device (for example, a sphygmomanometer or a pulsometer) via the network 200. The electronic medical record storage apparatus 300 acquires the time at which measurement is performed for the vital data together with the vital data and thus is able to store the vital data in association with the time of the measurement. Furthermore, the electronic medical record storage apparatus 300 is able to store the vital data in association with the time at which the vital data is acquired from the measurement device.

Exemplary vital data that is stored in the electronic medical record storage apparatus 300 will be described using FIG. 2. FIG. 2 is a diagram representing exemplary vital data according to the first embodiment. For example, a case where the electronic medical record storage apparatus 300 stores vital data in association with a time at which measurement is performed will be described below as an example.

For example, as illustrated in FIG. 2, the electronic medical record storage apparatus 300 stores items "patient ID", "type", "date and time of measurement" and "measured value" in association with one another as vital data. A "patient ID" represents information for identifying a patient about which vital data is measured. A "type" represents a type of vital data (such as a pulse rate, a blood pressure, a body temperature, a respiratory rate or SpO$_2$). A "date and time of measurement" represents a date and time when vital data is measured. A "measured value" represents a numerical value that is measured as vital data. For example, as illustrated in FIG. 2, the electronic medical record storage apparatus 300 stores a measured value "68" of a pulse rate of a patient P1, a measured value "141/89" of a blood pressure of the patient P1, and a measured value "36.5" of a temperature of the patient as vital data in association with a time "06/07/2017 09:15" at which the measurement is performed. For example, the electronic medical record storage apparatus 300 stores a measured value "59" of a pulse rate of a patient P2 and a measured value "131/81" of a blood pressure of the patient P2 as vital data in association with a time "06/14/2017 14:45" at which the measurement is performed.

The I/F circuitry 110 then receives the vital data from the electronic medical record storage apparatus 300 and outputs the received vital data to the processing circuitry 150. The control function 151 causes the vital data that is output from the I/F circuitry 110 to be stored in the memory 120. The control function 151 causes the vital data to be stored in the memory 120 in association with the time at which measurement is performed.

The display control function 152 then displays the vital data that is stored in the memory 120 in time series. Specifically, first, the display control function 152 acquires the vital data together with the date and time information from the memory 120. The display control function 152 displays the acquired vital data in time series based on the date and time information. Display of vital data in time series will be described using FIG. 3A. FIG. 3A is a diagram illustrating exemplary display of vital data in time series according to the first embodiment.

For example, the display control function 152 accepts an instruction to display the vital data in time series and specifying a patient from the doctor, nurse, or the like via the input interface 130. For example, a case where the patient P1 is specified will be described below as an example. The display control function 152 displays a line chart in which the vital data about the patient P is plotted in association with the time axis as illustrated in FIG. 3A, thereby displaying the vital data in time series. In other words, the display control function 152 displays a graph representing the vital data in time series. The graph represented in FIG. 3A is an exemplary first graph.

FIG. 3A illustrates a case where only pulse rates from among various types of vital data including heart rate, blood pressure, body temperature, respiratory rate and SpO$_2$ are displayed in time series. Alternatively, the display control function 152 may display multiple types of vital data in time series. The display control function 152 may accept specifying a type of vital data to be displayed in time series from the operator or may display a pre-set type of vital data in time series. Furthermore, the display control function 152 may accept changing the type of vital data to be displayed in time series from the operator. In an example, the display control function 152 accepts an operation to select a button represented in an area R1 in FIG. 3A from the operator, thereby changing the type of vital data to be displayed in time series.

A period for the vital data displayed in time series will be referred to as display period below. For example, in the case illustrated in FIG. 3A, "from April 27th to May 8th" is the display period. The display period may be the entire period during which the vital data about the patient P1 is measured or a period that is set by the operator. Furthermore, the display period can be changed by the operator optionally.

For example, the display control function 152 accepts setting a display period, such as "entire period", "from the current date and time until two weeks ago" or "from April 27th to May 8th", via the input interface 130. In an example, when the date on which measurement of heart rates of the patient P is started is "April 22th", the current date is "May 10th" and the operator sets a period "from April 27th to May 8th", the display control function 152 display the vital data corresponding to the period illustrated in FIG. 3A in time series.

The acquisition function 153 specifies a display period for the vital data displayed in time series as a period relating to the vital data displayed in time series. For example, as illustrated in FIG. 3A, the acquisition function 153 specifies "from April 27th to May 8th" as the display period. More specifically, as represented in FIG. 3B, the acquisition function 153 specifies a start time "4/27/2017 00:00:00" and an end time "5/08/2017 00:00:00" as the display period. FIG. 3B is a diagram for explaining the display period according to the first embodiment. In an example, the acquisition function 153 acquires a display period from the display control function 152 that controls output to the display 140 and specifies the acquired display period as the period relating to the vital data displayed in time series. In another example, the acquisition function 153 acquires a display period from a video card that controls display on the display 140, or the like, and specifies the acquired display period as the period relating to the vital data displayed in time series.

The calculation function 154 calculates statistical information from the vital data that is contained in the display period specified by the acquisition function 153. In other words, the calculation function 154 calculates statistical information from the vital data contained in the display period. Using FIGS. 4A and 4B, calculation of statistical information will be described. FIGS. 4A and 4B are diagrams for explaining calculation of statistical information according to the first embodiment. FIG. 4A represents vital data that corresponds to the entire period and that is obtained by measuring pulse rates of the patient P1.

First, the calculation function 154 extracts the vital data contained in the display period. For example, when the display period represented in FIG. 3B is acquired, the calculation function 154 acquires the vital data obtained by measurement from "4/27/2017 00:00:00" until "5/8/2017 00:00:00" from among the sets of vital data represented in FIG. 4A.

The calculation function 154 then calculates statistical information from the extracted vital data. The statistical information is information representing a tendency of vital data, such as a statistic based on the vital data. For example, the calculation function 154 calculates, as the statistical information, a distribution of the vital data contained in the period specified by the acquisition function 153 from the vital data that is extracted in FIG. 4A. For example, the calculation function 154 calculates, as the distribution of the vital data, the histogram data represented in FIG. 4B from the vital data that is extracted in FIG. 4A. Specifically, the calculation function 154 provides data intervals "TO 50", "TO 55", "TO 60", "TO 65", "TO 70" and "TO 75" for measured values of pulse rates and calculates the number (frequency) of measured values contained in the respective sections.

The display control function 152 then displays the statistical information that is calculated by the calculation function 154. For example, the display control function 152 displays the histogram data represented in FIG. 4B. In another example, the display control function 152 displays a distribution of the vital data graphically. For example, the display control function 152 displays a histogram based on the histogram data as the distribution of the vital data as represented in an area R2 in FIG. 5. FIG. 5 is a diagram illustrating exemplary display of statistical information according to the first embodiment. The histogram is an exemplary graph (second graph) representing a distribution of vital data.

As illustrated in FIG. 5, the display control function 152 displays the histogram in addition to the graph representing the vital data in time series. In other words, the display control function 152 simultaneously displays the first graph representing the vital data in time series and the second graph representing the distribution of the vital data.

As illustrated in FIG. 5, the display control function 152 displays the graph representing the vital data in time series and the histogram such that the vertical axis representing the pulse rate is shared. In other words, the display control function 152 displays the first graph representing the vital data in time series and the second graph representing the distribution of the vital data such that at least one axis of the first graph and the second graph are associated each other.

FIG. 5 illustrates the case where only the histogram about the measured value of pulse rates is displayed. The detection function 155 may detect an operation to change the type of vital data to be displayed according to an operation performed by the operator. For example, when an operation to select "blood pressure" in the area R1 is detected, the calculation function 154 calculates histogram data about measured values of blood pressures contained in the display period and the display control function 152 displays a histogram (histogram of the blood pressures) as the distribution of the vital data. The display control function 152 may display the blood pressure histogram instead of the histogram (pulse rate histogram) represented in the area R2 in FIG. 5, superimpose and display the blood pressure histogram on the pulse rate histogram or display the blood pressure histogram in a position different from that of the area R2. The display control function 152 may switch between displaying the histogram and not displaying the histogram according to whether the check box represented in an area R3 in FIG. 5 is checked.

Figure 6:
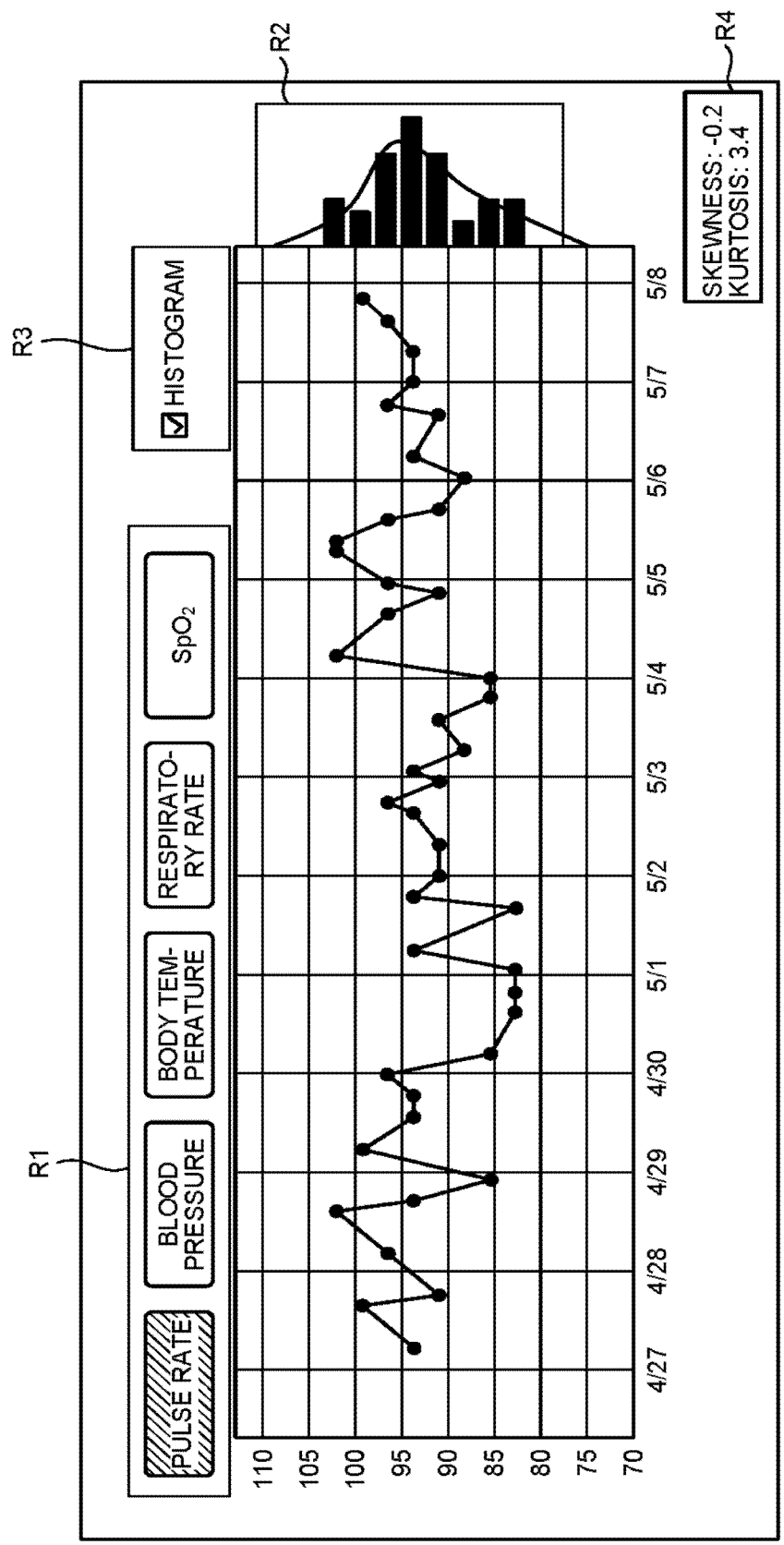
FIG. 6 is a diagram illustrating exemplary display of statistical information according to the first embodiment.

The display control function 152 may display the histogram and display a statistic about the histogram as the statistical information. For example, the calculation function 154 calculates histogram data from the vital data and calculates a skewness and a kurtosis. As illustrated in FIG. 6, the display control function 152 displays the histogram in the area R2 and displays the skewness and kurtosis in an area R4. FIG. 6 is a diagram illustrating exemplary display of statistical information according to the first embodiment.

When the acquisition function 153 specifies multiple display periods, the display control function 152 may display histograms that are generated for the respective multiple display periods. The case where the acquisition function 153 specifies multiple display periods is, for example, a case where the display period is changed according to an operation performed by the operator and thus the acquisition function 153 specify display periods before and after the change.

In an example, first, the operator performs an operation to change the display period of displaying in time series. In other words, the operator who refers to the vital data that is displayed in time series shortens the display period to enlarge part of the data for observation, increase the display period for observing a longer period or scrolls the display period for observing another period. The operation of changing the display period includes, for example, an operation on a mouse or a tablet of the input interface 130.

Specifically, the operator scrolls the display period by performing a wheel operation on the mouse. For example, the operator performs a wheel operation on the mouse while pressing a given key of the keyboard to extend the display period or shorten the display period. For example, the operator scrolls the display period by performing a swipe operation on the tablet. For example, the operator extends the display period or shortens the display period by performing a pinch-in/pinch-out operation on the tablet.

The display control function 152 then changes the display period for displaying vital data in time series. The detection function 155 detects an operation to change the display period. The acquisition function 153 specifies the changed display period as the period relating to the vital data displayed in time series. For example, while the operator is scrolling the display period, the acquisition function 153 sequentially specifies display periods that are changed sequentially. Each time a display period is specified, the calculation function 154 calculates histogram data from the vital data contained in the display period. Each time histogram data is calculated, the display control function 152 generates a histogram and displays the histogram. For example, the display control function 152 replaces the already displayed histogram with the newly generated histogram to display the newly generated histogram or displays the already displayed histogram and the newly generated histogram side by side.

For example, the display control function 152 superimposes and displays the histograms that are generated for the respective display periods. In an example, the display control function 152 superimposes and displays a newly generated histogram and a histogram that is generated a given time (for example, five seconds) before as illustrated in the area R2 in FIG. 7. FIG. 7 is a diagram illustrating exemplary display of statistical information according to the first embodiment.

The display control function 152 may, when superimposing and displaying multiple histograms, give a simplified display of the histograms using polygonal lines or curves. The display control function 152 may give a display such that, as illustrated in the area R2 in FIG. 7, clearness of a histogram generated in the past is larger than that of the newly generated histogram. The clearness of the histogram is a parameter that has an effect on visibility of the histogram. For example, the clearness of the histogram may include, in addition to how transparent the histogram is, the thickness of the line representing the histogram and intervals in a dashed line or a dotted line.

The display control function 152 displays the histograms that are generated for the respective display periods side by side. In an example, the display control function 152 displays a histogram that is newly generated, a histogram generated five seconds before, a histogram generated 10 seconds before and a histogram generated 15 seconds before side by side.

When multiple histograms are displayed, the display control function 152 may standardize the histograms according to the number of sets of vital data that are used to generate each of the histograms and then display the histograms. For example, when the number of sets of vital data used to generate the solid-line histogram in FIG. 7 is "20" and the number of sets of vital data used to generate the dashed-line histogram in FIG. 7 is "10", the display control function 152 doubles the height of the dashed-line histogram and then displays the histogram in the area R2. In other words, the display control function 152 may display histograms according to percentages (ratios) according to the number of sets of vital data contained in each period.

The display control function 152 may display a difference between histograms that are generated for multiple periods, respectively. For example, as for FIG. 7, the calculation function 154 calculates a difference in the number of measured values for each data interval (frequency) between the vital data that is used to generate the solid-line histogram and the vital data that is used to generate the dashed-line histogram. The display control function 152 displays the calculated difference as a histogram as the difference between the histograms. The display control function 152 may superimpose and display the difference on the solid-line histogram and the dashed-line histogram represented in FIG. 7 or may display the difference instead of the solid-line histogram and the dashed-line histogram.

The display control function 152 may display a result of examining a difference between histograms that are generated for the multiple periods, respectively. For example, as for FIG. 7, the calculation function 154 uses the vital data used to generate the solid-line histogram and the vital data used to generate the dashed-line histogram to examine a difference between the histogram, using a significance probability P of "0.15", and displays the result of the examination.

Furthermore, the display control function 152 may give the displays represented in FIGS. 5 to 7 together with various types of information. For example, the display control function 152 may further display an image relating to the patient P1. In an example, the display control function 152 gives the displays represented in FIGS. 5 to 7, etc., simultaneously with a list screen on which medical images acquired from the patient P1 or icons (such as thumbnails) representing the medical images are arranged in time series. In an example, the display control function 152 gives the displays represented in FIGS. 5 to 7, etc., simultaneously with a list screen on which medical reports on the patient P1 or icons representing the medical reports are arranged in time series.

In the above-described example, the case where histogram data, etc., are calculated as statistical information is described; however, embodiments are not limited thereto. For example, the calculation function 154 calculates various statistics represented in FIG. 8A as statistical information from the vital data in FIG. 4A that is extracted. FIG. 8A is a diagram for explaining calculation of statistical information according to the first embodiment. For example, as illustrated in FIG. 8A, the calculation function 154 calculates an average, a standard error, a median, standard deviation, a variance, a kurtosis, a skewness, a range, a minimum, a maximum, a sum, a number of samples, etc., of the vital data contained in the display period. The display control function 152 then displays the statistical information that is calculated by the calculation function 154. For example, the display control function 152 displays the statistics represented in FIG. 8A as statistical information on the display 140.

The calculation function 154 may calculate statistical information of the vital data contained in the display period using the display period as a unit or may calculate the statistical information for each of segments of time obtained by segmenting the display period at each unit of time. For example, when "April 27th~May 8th" is the display period, the calculation function 154 may calculate statistical information about the vital data from April 27th to May 8th or calculate statistical information for each segment of time, such as "a day" or "a week".

Figure 8B:
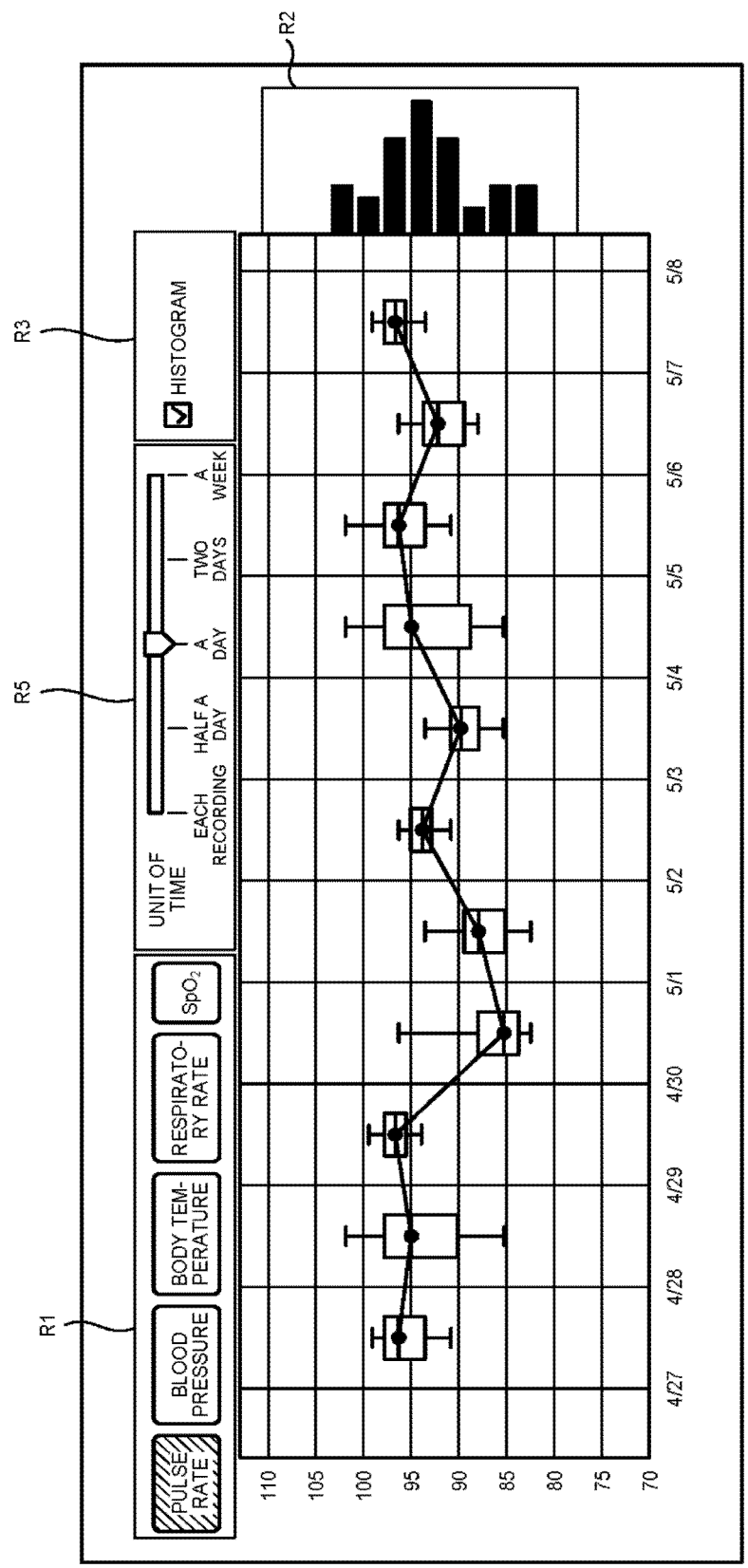
FIG. 8B is a diagram illustrating exemplary display of statistical information according to the first embodiment.

For example, the calculation function 154 segments the display period at each "day" and calculates a distribution of vital data for each "day". In an example, the calculation function 154 calculates, for each "day", a minimum, a lower quartile, a median, an upper quartile and a maximum as the distribution of the vital data. The display control function 152 then graphically displays the distributions of the vital data each for each "day" in time series. For example, as illustrated in FIG. 8B, the display control function 152 displays the distributions of the vital data each for each "day" as box plots (box-and-whisker plots) in time series. Specifically, the display control function 152 generates, for each day of the display period, a box plot consisting of whiskers representing minimum to maximum values, a box representing the lower to upper quartiles and a divider inside the box representing a median and displays the box plots in association with the time axis. FIG. 8B is a diagram illustrating exemplary display of statistical information according to the first embodiment.

FIG. 8B represents the box plots each based on the distribution of the vital data calculated for each "day"; however, any unit of time may be used to calculate the distribution of the vital data. The unit of time may be changed according to an operation performed by the operator. For example, as illustrated in an area R5 in FIG. 8, the display control function 152 displays a bar representing units of time including "each recording", "half a day", "a day", "two days" and "a week" and a pointer that slides on the bar. The detection function 155 accepts an operation to slide the pointer from the operator via the input interface 130 and thus detects the operation of changing the unit of time.

Except for the case where the unit of time is changed to "each recording", the calculation function 154 segments the display period at each unit of time after the change and calculates a distribution of the vital data for each segment of time. The display control function 152 then displays the box plots each for each unit of time after the change as the distribution of the vital data for each segment of time. On the other hand, when the unit of time is changed to "each recording", the display control function 152 displays the vital data in time series by a line chart.

The unit of time according to which the distribution of the vital data is calculated may be calculated by the calculation function 154 according to the display period. For example, the calculation function 154 calculates a unit of time such that a predetermined given number of box plots (for example, 10 to 15 box plots) are displayed. In other words, the calculation function 154 calculates a unit of time according to granularity of display. In an example, in the case where the display period is "April 27th~May 8th", when the unit of time is "half a day", there are "22" box plots; when the unit of time is "a day", there are "11" box plots; and when the unit of time is "two days", there are "6" box plots. Accordingly, when the display period is "April 27th May 8th", the calculation function 154 calculates "a day" as the unit of time and calculates a distribution of the vital data for each "day".

FIG. 8B represents box plots as exemplary display of distributions of the vital data calculated for the segments of time, respectively; however, embodiments are not limited thereto. For example, the display control function 152 may display the distributions of the vital data for the respective segments of time, in time series, using a diagram representing an average and an error bar (bar having a length corresponding to a standard deviation or the like), a candle chart or a line chart.

Furthermore, the periods of the segments may overlap each other. As for the periods of the segments overlapping each other, a case where the display period is "August 3rd~August 6th", the unit of time is "a day" and a "kurtosis" is calculated as a distribution of vital data will be described as an example. First of all, the display control function 152 displays vital data corresponding to "August 3rd~August 6th" in time series and the acquisition function 153 specifies "August 3rd~August 6th" as a display period.

The calculation function 154 then acquires segments of time overlapping each other. For example, the calculation function 154 segments the display period at each "day" and acquires, as the segments of time overlapping each other, a time consisting of each of the days of the display period and days preceding and following the day. In other words, the calculation function 154 acquires four segments of time "August 2nd~August 4th", "August 3nd~August 5th", "August 4th~August 6th" and "August 5th~August 7th".

The calculation function 154 then calculates, for each of the segments of time, a "kurtosis" from the vital data contained in the segment of time. The display control function 152 then displays the "kurtoses" for the segments of time in time series. For example, the display control function 152 displays the "kurtoses" for the respective segments of time in time series by a line chart in which the kurtosis calculated for "August 2nd~August 4th" is plotted at the position of "August 3rd", the kurtosis calculated for "August 3nd~August 5th" is plotted at the position of "August 4th", the kurtosis calculated for "August 4th~August 6th" is plotted at the position of "August 5th" and the kurtosis calculated for "August 5th~August 7th" is plotted at the position of "August 6th".

Figure 9:
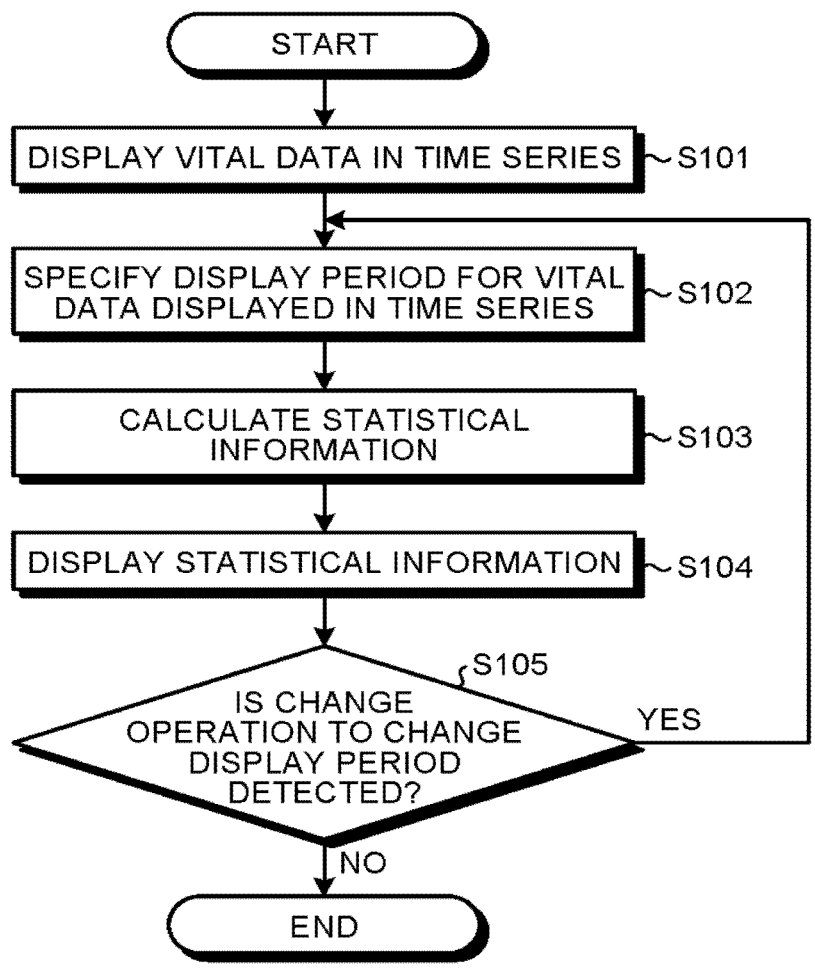
FIG. 9 is a flowchart for explaining a flow of a process performed by the medical information processing system according to the first embodiment.

An exemplary procedure of a process performed by the medical information processing system 1 will be described using FIG. 9. FIG. 9 is a flowchart illustrating a flow of a series of steps implemented by the medical information processing system 1 according to the first embodiment. Step S101 and step S104 are steps corresponding to the display control function 152. Step S102 is a step corresponding to the acquisition function 153. Step S103 is a step corresponding to the calculation function 154. Step S105 is a step corresponding to the detection function 155.

First, the processing circuitry 150 reads vital data from the memory 120 and displays the vital data in time series (step S101). The processing circuitry 150 then specifies a display period for the vital data displayed in time series as a period relating to the vital data displayed in time series (step S102). The processing circuitry 150 then calculates statistical information from the vital data contained in the display period (step S103). For example, the processing circuitry 150 calculates a distribution of the vital data contained in the display period. The processing circuitry 150 then displays the calculated statistical information on the display 140 (step S104). For example, the processing circuitry 150 graphically displays the distribution of the vital data by a histogram, a box plot chart, or the like.

The processing circuitry 150 determines whether a change operation to change the display period is detected (step S105). When the change operation is detected (YES at step S105), the processing circuitry 150 moves to step S102 again. On the other hand, when the change operation is not detected (NO at step S105), the processing circuitry 150 ends the process.

As described above, according to the first embodiment, the display control function 152 acquires the vital data together with date and time information associated with the vital data. The display control function 152 displays the vital data in time series based on the date and time information. The acquisition function 153 specifies a display period for the vital data displayed in time series as the period relating to the vital data displayed in time series. The calculation function 154 calculates statistical information from the vital data contained in the display period. Furthermore, the display control function 152 displays the calculated statistical information. Accordingly, the medical information processing system 1 according to the first embodiment is able to represent the statistical information about the displayed vital data to the operator and make it easy to understand the data tendency. Furthermore, the medical information processing system 1 is able to make it easy to understand the condition of the patient and determine a type and dose of drug by making it easy to understand the data tendency.

According to the first embodiment, the calculation function 154 calculates a distribution of vital data contained in a display period. The display control function 152 graphically displays the distribution of the vital data by a histogram, a box plot chart, or the like. Accordingly, the medical information processing system 1 according to the first embodiment is able to represent the distribution of the displayed vital data graphically and make it easier to understand data tendency.

According to the first embodiment, the detection function 155 detects a change operation to change the display period. The acquisition function 153 specifies the changed display period as a period relating to the vital data displayed in time series. The calculation function 154 calculates statistical information from the vital data contained in the changed display period. The display control function 152 further displays the calculated statistical information. Accordingly, the medical information processing system 1 according to the first embodiment is able to dynamically display the statistical information corresponding to the display period and make it easier to understand data tendency.

According to the first embodiment, the display control function 152 displays the first graph that represents the vital data in time series and the second graph that represents the distribution of the vital data such that at least one axis of the first graph and the second graph are associated each other. Accordingly, compared to the case where the first graph and the second graph are displayed independently, the medical information processing system 1 according to the first embodiment is able to give a representation such that the meaning and content of the second graph with respect to the first graph is easily understandable and make it easier to understand data tendency.

The above-described first embodiment illustrates the case where the acquisition function 153 specifies a display period as a period relating to the vital data displayed in time series. On the other hand, the second embodiment illustrates a case where the acquisition function 153 specifies a specified period that is specified in a display period as a period relating to vital data displayed in time series.

The medical information processing system 1 according to a second embodiment has the same configuration as that of the medical information processing system 1 illustrated in FIG. 1 and is different from the medical information processing system 1 illustrated in FIG. 1 in part of the processes performed by the display control function 152, the acquisition function 153, the calculation function 154 and the detection function 155. As for the aspect that the medical information processing system 1 according to the second embodiment has the same configuration as that of the first embodiment described above, descriptions thereof will be omitted by denoting the same components with the same reference numbers as those in FIG. 1.

Figure 10:
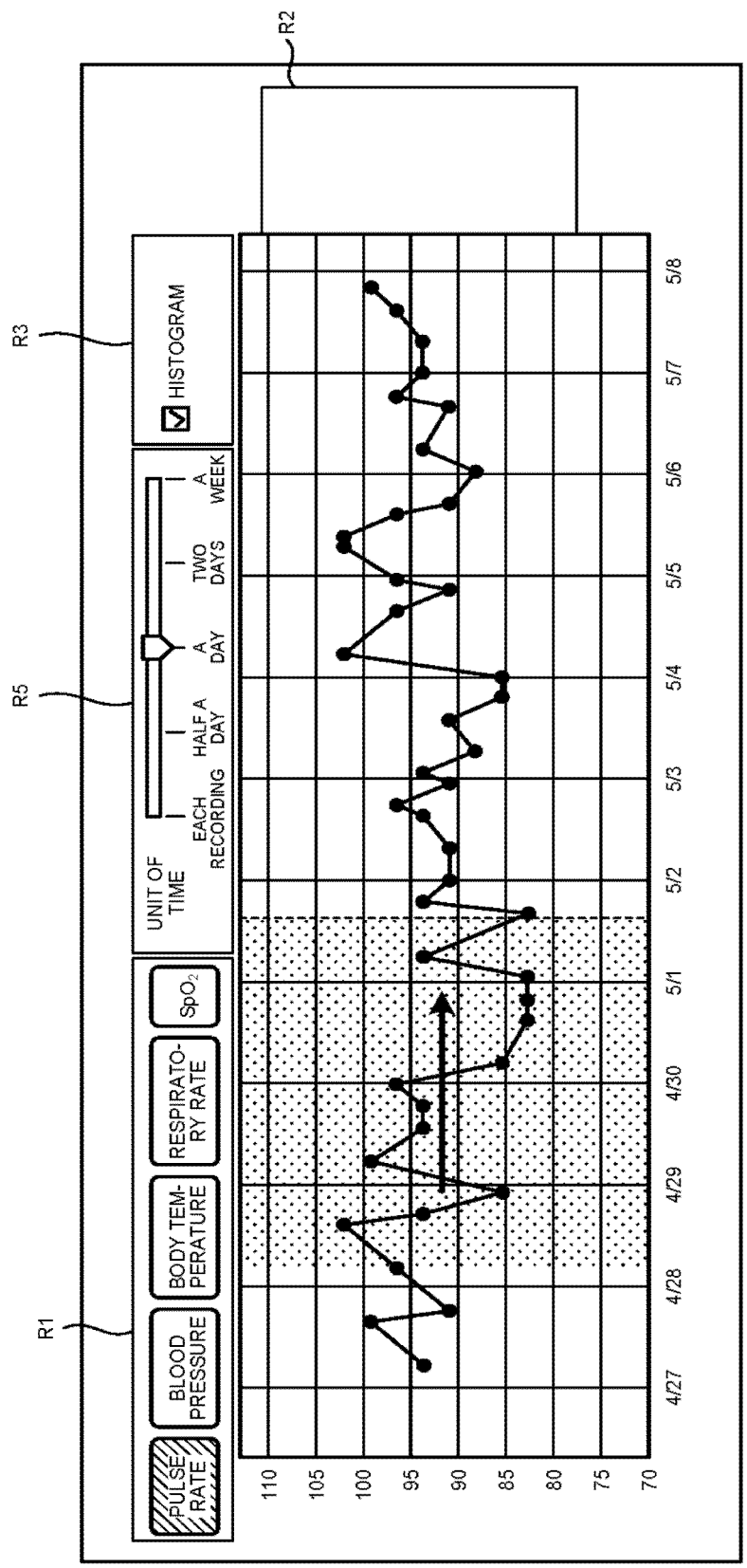
FIG. 10 is a diagram for explaining a specified period according to a second embodiment.

First, the display control function 152 acquires vital data together with date and time information associated with the vital data. The display control function 152 displays the acquired vital data in time series based on the date and time information. For example, the display control function 152 causes the display 140 to display a line chart in which the measured values of pulse rates of the patient are plotted in association with the time axis as illustrated in FIG. 10, thereby displaying the vital data in time series. FIG. 10 is a diagram for explaining a specified period according to the second embodiment.

FIG. 10 illustrates the case where the vital data is displayed in time series by a line chart; however, embodiments are not limited thereto. For example, the display control function 152 may display the vital data in time series by a box plot chart, or the like, instead of a line chart. The display control function 152 may display, in addition to a line chart, a box plot chart, or the like, statistical information (such as a histogram) that is calculated from vital data that is contained in the display period.

The detection function 155 then detects an operation to specify a specified period in a display period. For example, the detection function 155 detects an operation to specify the specified period, which is represented in FIG. 10, via an operation on the mouse, tablet, or the like, of the input interface 130. The acquisition function 153 acquires the specified period based on the operation that is detected by the detection function 155 and specifies the specified period as a period relating to the vital data displayed in time series.

Figures 11A, 11B, 11C:
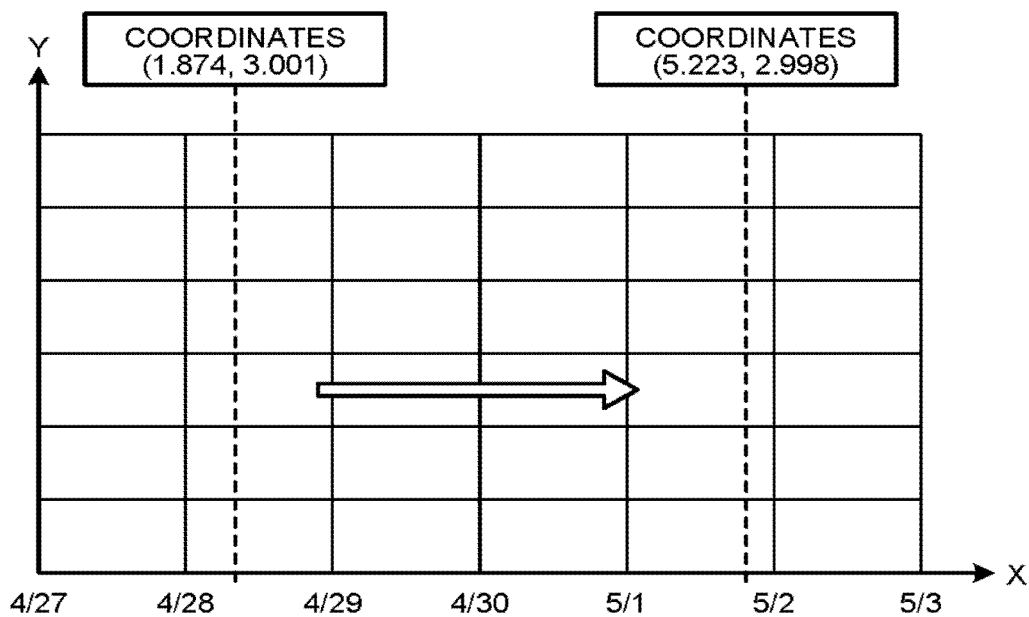
FIG. 11A is a diagram for explaining the specified period according to the second embodiment.
FIG. 11B is a diagram for explaining the specified period according to the second embodiment.
FIG. 11C is a diagram for explaining the specified period according to the second embodiment.

The specified period will be described using FIGS. 11A, 11B and 11C. FIGS. 11A, 11B and 11C are diagrams for explaining a specified period according to the second embodiment. FIG. 11A is diagram of an enlarged part of the display of the vital data in time series illustrated in FIG. 10, where the X-axis represents time and Y-axis represents pulse rate measured values.

First of all, an operator performs an operation to specify two points in the coordinate system in FIG. 11A via the input interface 130. For example, the operator operates the mouse of the input interface 130 to start drag in the position of the set of coordinates (1.874, 3.001) and performs drop in the position of the set of coordinates (5.223, 2.998). In this case, the detection function 155 detects that an operation to start drag at the set of coordinates (1.874, 3.001) and an operation to perform drop at the set of coordinates (5.223, 2.998) are performed.

As represented in FIG. 11B, the acquisition function 153 acquires the X-axis (time axis) coordinates and the operation content from the operations that are detected by the detection function 155. The acquisition function 153 converts the X-axis (time axis) coordinates into times and converts the operation content into display meanings as represented in FIG. 11C and thus acquires a specified period. For example, as represented in FIG. 11C, the acquisition function 153 acquires a start time "4/28/2017 06:24:15" and an end time "5/1/2017 22:15:33" as the specified period. Furthermore, the acquisition function 153 specifies the acquired specified period as a period relating to the vital data displayed in time series.

The calculation function 154 calculates statistical information from vital data that is contained in the specified period and the display control function 152 displays the calculated statistical information. For example, the calculation function 154 calculates a distribution of the vital data contained in the specified period and displays the distribution of the vital data graphically. In an example, the calculation function 154 calculates histogram data as the distribution of the vital data from the vital data contained in the specified period and the display control function 152 displays the histogram data, a histogram based on the histogram data, and statistics (such as skewness and freshness) relating to the histogram.

When the acquisition function 153 specifies multiple specified periods, the display control function 152 may display histograms that are generated for the respective multiple specified periods. The case where the acquisition function 153 specifies multiple specified periods is, for example, a case where multiple specified periods are specified according to operations performed by the operator.

For example, the display control function 152 replaces an already displayed histogram with a newly generated histogram to display the newly generated histogram. For example, the display control function 152 superimposes and displays histograms that are generated for respective specified periods. The display control function 152 may, when displaying multiple histograms in a superimposed manner, give a simplified display of the histograms using polygonal lines or curves or may give a display such that clearness of a histogram generated in the past is larger.

Figure 12:
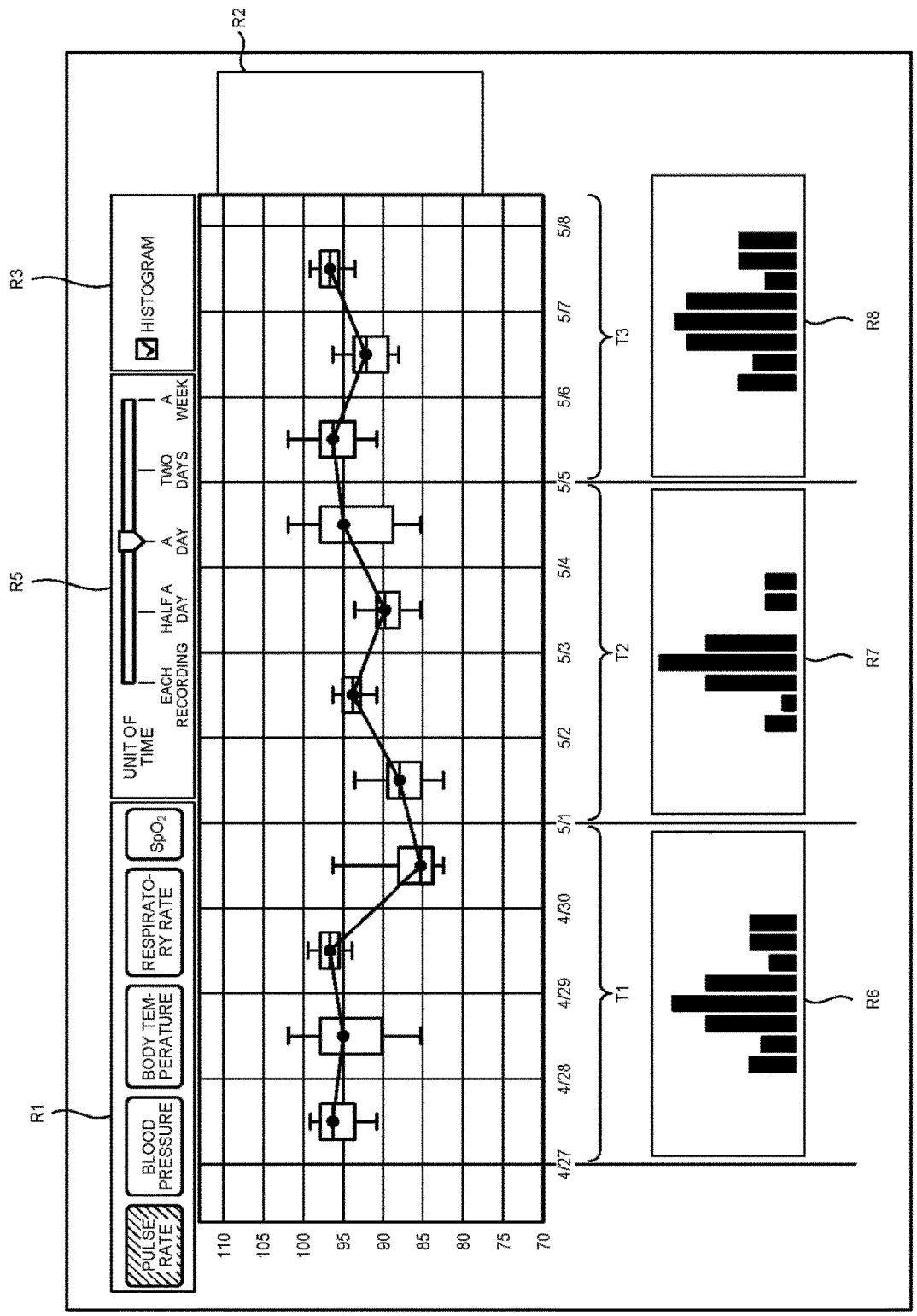
FIG. 12 is a diagram illustrating exemplary display of statistical information.

For example, the display control function 152 displays the histograms that are generated for the respective specified periods side by side. In an example, as illustrated in FIG. 12, when the acquisition function 153 acquires a period T1, a period T2 and a period T3 as specified periods, the display control function 152 displays histograms that are generated for the respective periods T1, T2 and T1 in an area R6, an area R7 and an area R8, respectively. FIG. 12 is a diagram illustrating exemplary display of statistical information according to the second embodiment.

For example, the calculation function 154 calculates a statistic as statistical information from the vital data contained in the specified period and the display control function 152 displays the statistic. For example, the calculation function 154 calculates statistical information for each of segments of time obtained by segmenting the specified period at each unit of time and the display control function 152 displays the sets of statistical information for the respective segments of time in time series by a box plot chart, or the like.

In an example, when vital data is displayed in time series by a line chart where the unit of time is "each recording", the calculation function 154 segments the specified period at each "day" and calculates a minimum, a lower quartile, a median, an upper quartile and a maximum as statistical information of the vital data for each day. As for the specified period in the display period, the display control function 152 displays sets of statistical information for the respective days in time series as box plots and, as for the period obtained by excluding the specified period from the display period, displays the vital data in time series by a line chart where the unit of time is "each recording".

In another example, when sets of vital data are displayed in time series by a box plot chart where the unit of time is "a day", the calculation function 154 calculates a minimum, a lower quartile, a median, an upper quartile and a maximum as statistical information of the vital data in the specified period. As for the specified period, the display control function 152 displays a box plot diagram and, as for the period obtained by excluding the specified period from the display period, gives a display of a box plot chart in time series, where the unit of time is "a day".

Figure 13:
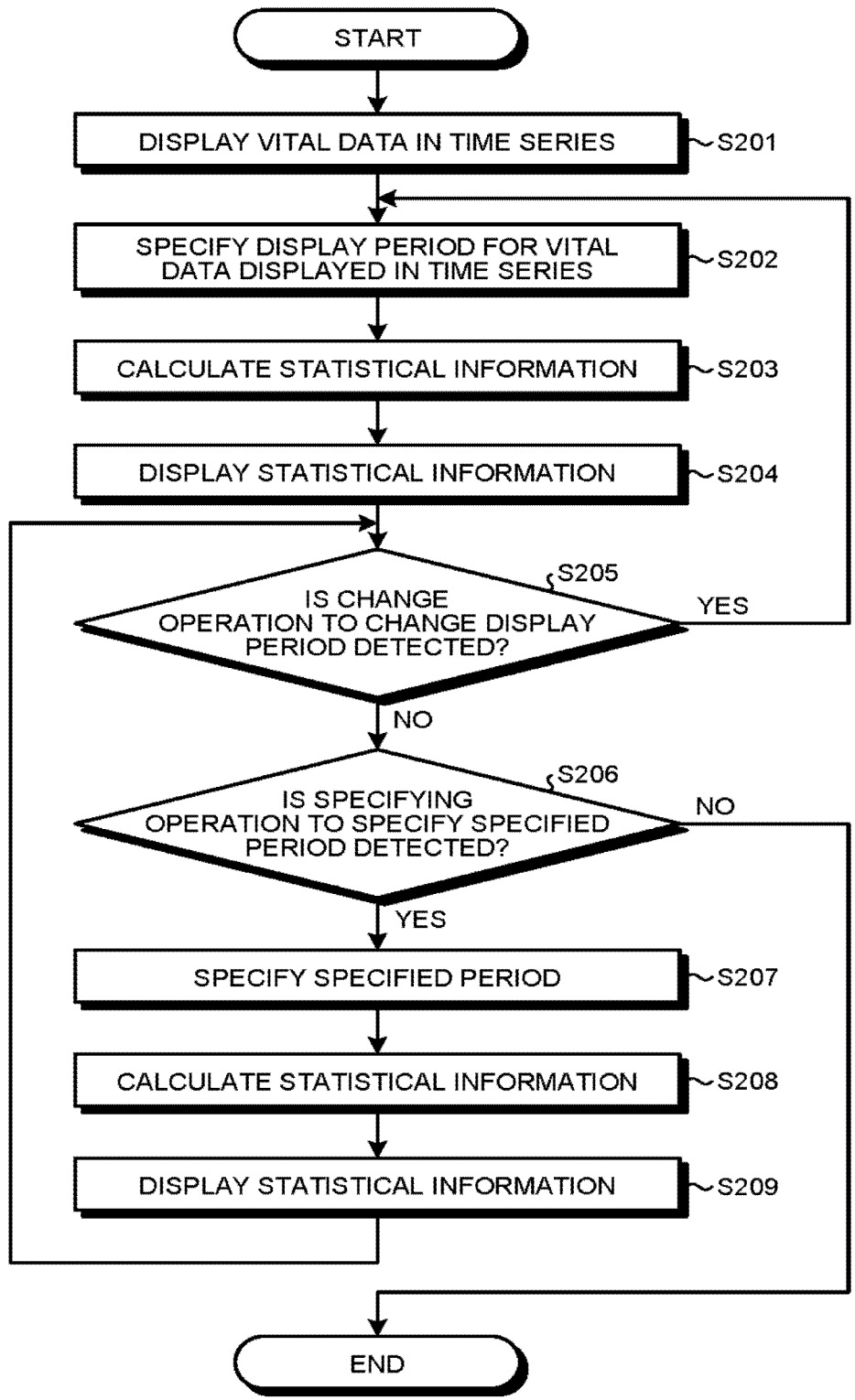
FIG. 13 is a flowchart for explaining a flow of processes performed by a medical information processing system according to the second embodiment.

An exemplary procedure of a process performed by the medical information processing system 1 will be described using FIG. 13. FIG. 13 is a flowchart illustrating a flow of a series of steps implemented by the medical information processing system 1 according to the second embodiment. Step S201, S204 and S209 are steps corresponding to the display control function 152. Steps S202 and S207 are steps corresponding to the acquisition function 153. Steps S203 and S208 are steps corresponding to the calculation function 154. Steps S205 and S206 are steps corresponding to the detection function 155.

First, the processing circuitry 150 reads vital data from the memory 120 and displays the vital data in time series (step S201). The processing circuitry 150 then specifies a display period for the vital data that is displayed in time series as a period relating to the vital data displayed in time series (step S202). The processing circuitry 150 then calculates statistical information from the vital data contained in the display period (step S203). For example, the processing circuitry 150 calculates a distribution of the vital data contained in the display period. The processing circuitry 150 then displays the calculated statistical information on the display 140 (step S204). For example, the processing circuitry 150 graphically displays the distribution of the vital data by a histogram, a box plot chart, or the like.

The processing circuitry 150 determines whether a change operation to change the display period is detected (step S205). When the change operation is detected (YES at step S205), the processing circuitry 150 moves to step S202 again. On the other hand, when the change operation is not detected (NO at step S205), the processing circuitry 150 determines whether a specifying operation to specify a specified period is detected (step S206).

When the specifying operation is detected (YES at step S206), the processing circuitry 150 specifies the specified period as a period relating to the vital data displayed in time series (step S207). The processing circuitry 150 then calculates statistical information from the vital data contained in the specified period (step S208). For example, the processing circuitry 150 calculates a distribution of the vital data contained in the specified period. The processing circuitry 150 then displays the calculated statistical information on the display 140 (step S209). For example, the processing circuitry 150 graphically displays the distribution of the vital data by a histogram, a box plot chart, or the like. After step S209, the processing circuitry 150 moves to step S205 again. On the other hand, when the specifying operation is not detected (NO at step S206), the processing circuitry 150 ends the process.

As described above, according to the second embodiment, the detection function 155 detects a specifying operation to specify a specified period in the display period for the vital data that is displayed in time series as a period relating to the vital data displayed in time series. The acquisition function 153 specifies the specified period as a period relating to the vital data displayed in time series. The calculation function 154 calculates statistical information from the vital data contained in the specified period. The display control function 152 further displays the calculated statistical information. Accordingly, the medical information processing system 1 according to the second embodiment displays the statistical information for the displayed vital data in a range desired by the operator, thereby being able to make it easy to understand data tendency.

According to the second embodiment, the calculation function 154 calculates a distribution of the vital data that is contained in the specified period. The display control function 152 graphically displays the distribution of the vital data by a histogram, a box plot chart, or the like. Accordingly, the medical information processing system 1 according to the second embodiment is able to represent the distribution of the specified vital data graphically and make it easier to understand data tendency.

The detection function 155 may detect the drag and drop operations illustrated in FIG. 11A as the change operation to change the display period. In this case, as illustrated in FIG. 11B, the acquisition function 153 acquires X-axis (time axis) coordinates and operation content from operations that are detected by the detection function 155. As illustrated in FIG. 11C, the acquisition function 153 acquires a start time "4/28/2017 06:24:15" and an end time "5/1/2017 22:15:33" as the display period after change. Furthermore, the acquisition function 153 specifies the display period after change as a period relating to the vital data displayed in time series. The calculation function 154 then calculates statistical information from vital data that is contained in the display period after change and the display control function 152 displays a histogram, a box plot chart, or the like, as statistical information.

In a third embodiment, variations of display of statistical information will be described. The medical information processing system 1 according to the third embodiment has the same configuration as that of the medical information processing system illustrated in FIG. 1 and is different from the medical information processing system 1 illustrated in FIG. 1 in part of the processes performed by the display control function 152 and the calculation function 154. As for the aspect that the medical information processing system 1 according to the third embodiment has the same configuration as that of the first embodiment described above, descriptions thereof will be omitted by denoting the same components with the same reference numbers as those in FIG. 1.

Figure 14A:
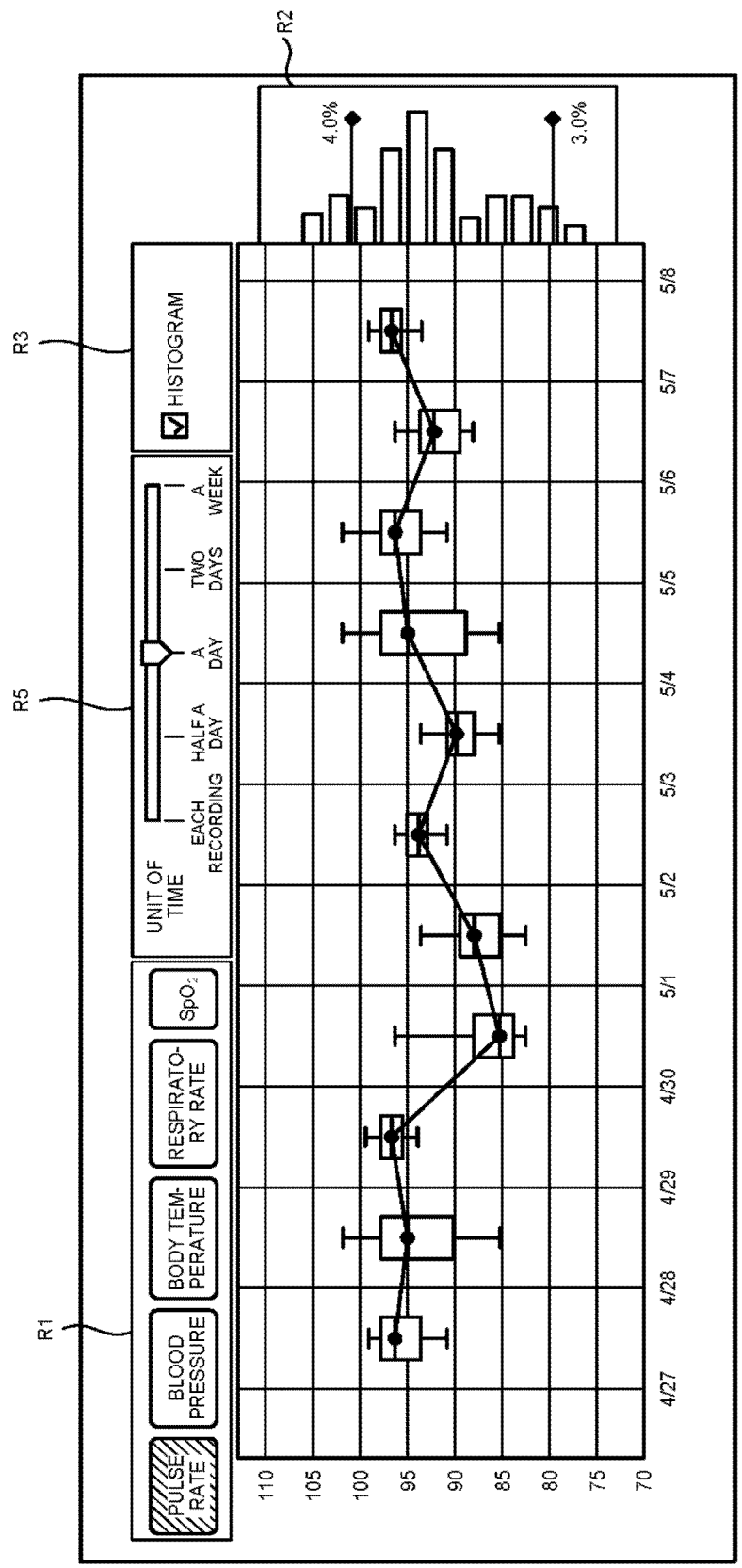
FIG. 14A is a diagram illustrating exemplary display of statistical information according to a third embodiment.
Figure 14B:
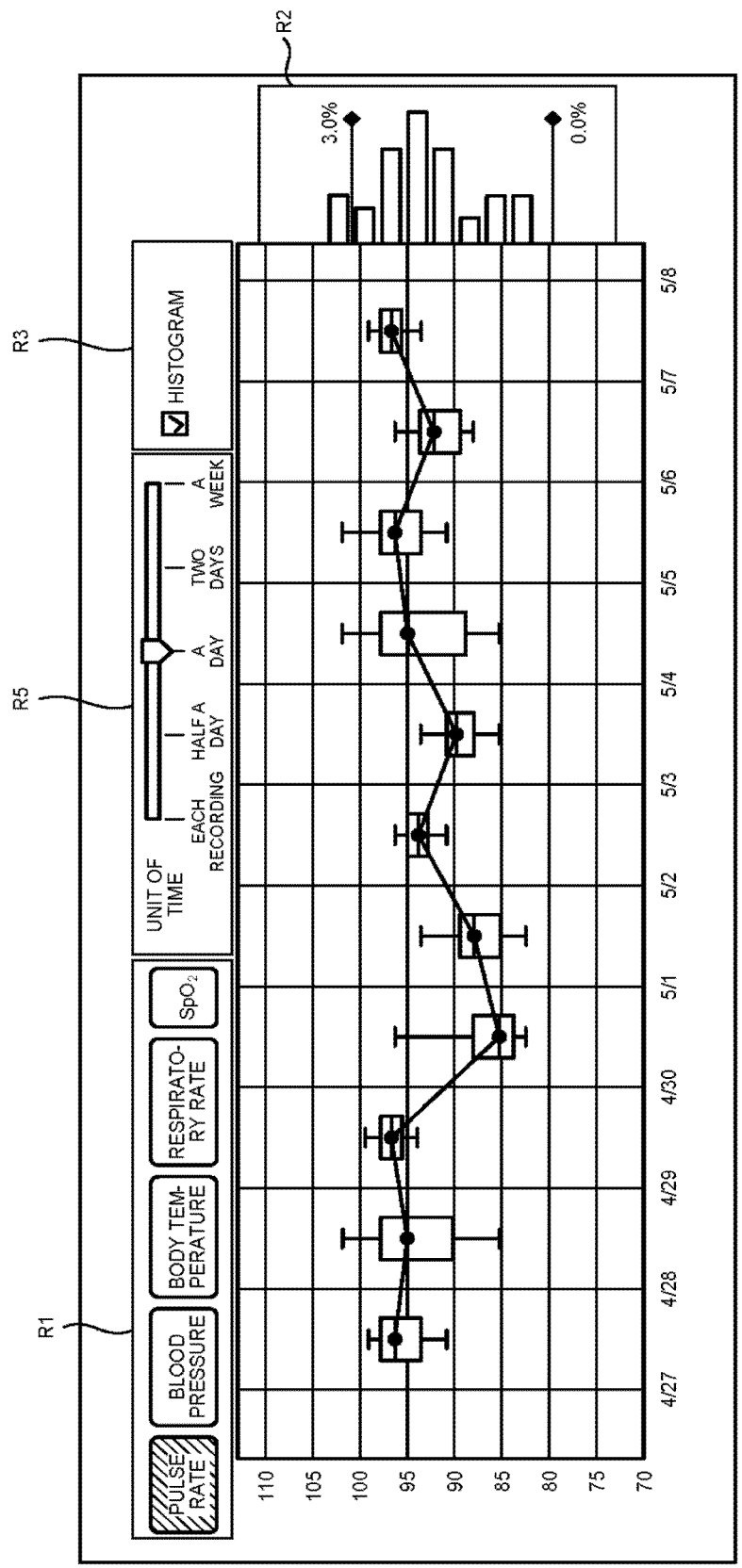
FIG. 14B is a diagram illustrating exemplary display of statistical information according to the third embodiment.

With reference to FIGS. 14A and 14B, exemplary display of statistical information according to the third embodiment will be described. FIGS. 14A and 14B are diagrams illustrating exemplary display of statistical information according to the third embodiment.

First of all, the calculation function 154 calculates histogram data from vital data contained in a display period. The display control function 152 displays a histogram based on the histogram data as represented in the area R2 in FIG. 14A. The display control function 152 further displays thresholds as represented in the area R2 in FIG. 14A.

The thresholds represent whether the values of vital data are within a normal range. For example, the case illustrated in FIG. 14A represents that "101" and "79" serve as thresholds, a percentage of pulse rate measured values equal to or larger than "101" in the display period is "4.0%" and a percentage of pulse rate measured values equal to or smaller than "79" in the display period is "3.0%". In other words, by representing the thresholds, the display control function 152 is able to represent to what extent the vital data is within a normal range.

The thresholds may be calculated by the calculation function 154 based on the vital data. For example, the calculation function 154 calculates standard deviations for measured values in the entire period, for measured values in the display period, and for measured values in the specified period from among the pulse rate measured values that are calculated about the patient P1 and calculates "100(+2σ)" and "79(−2σ)" as thresholds. The display control function 152 displays "100(+2σ)" and "79(−2σ)" as thresholds as illustrated in FIG. 14B. The display control function 152 further gives a display indicating that a percentage of measured values over "100(+2σ)" in the display period is "3.0%" and a percentage of measured values under "79(−2σ)" in the display period is "0.0%". By displaying the thresholds that are calculated based on the vital data, the display control function 152 is able to dynamically represent to what extent the vital data is within a normal range.

When an abnormal value resulting from an error in measurement or input is contained in the vital data, the display control function is able to let the operator to know the containment of the abnormal value. For example, the calculation function 154 calculates a standard deviation for the pulse rate measured values that are measured about the patient P1 and calculates pulse rates corresponding to "+3σ" and pulse rates corresponding to "−3σ" as thresholds. The display control function 152 is able to represent, to the operator, a measured value out of a range "±3σ" as an abnormal value resulting from an error in measurement or input.

FIGS. 14A and 14B illustrate the case where thresholds are displayed on a histogram as a method of displaying a result of comparison between vital data and thresholds; however, embodiments are not limited thereto. For example, the display control function 152 may display thresholds on the right side of the graph represented in FIG. 14A or 14B (on the vertical axis) or on the graph. For example, the display control function 152 may display thresholds by numerical values. For example, the display control function 152 may display whether the vital data contains a value over a threshold or a value under a threshold. For example, the display control function 152 may display a percentage or number of sets of vital data over a threshold or vital data under a threshold.

Figure 15:
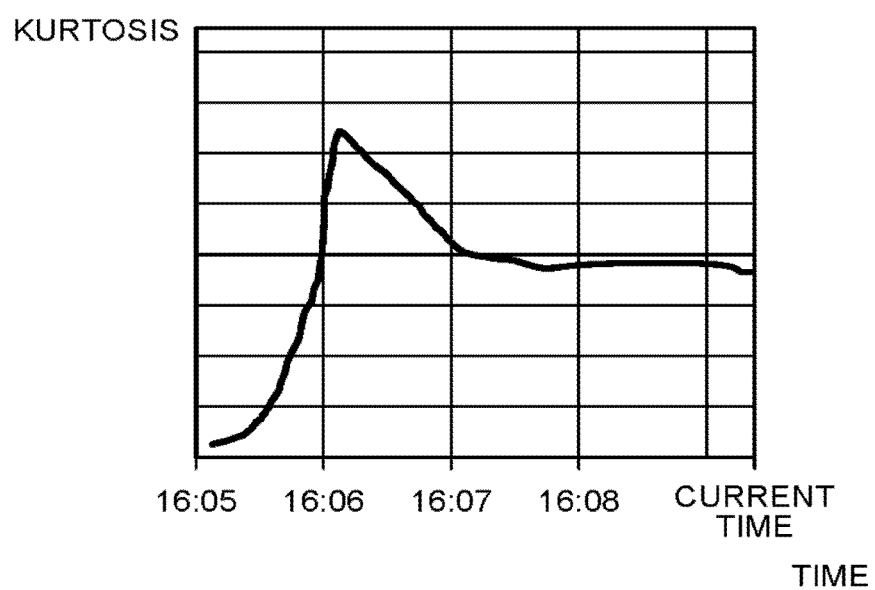
FIG. 15 is a diagram illustrating exemplary display of statistical information according to the third embodiment.

With reference to FIG. 15, other exemplary display of statistical information according to the third embodiment will be described. FIG. 15 is a diagram illustrating exemplary display of statistical information according to the third embodiment.

First of all, the calculation function 154 calculates a statistic each time a display period or a specified period is specified. For example, when the operator is scrolling the display period sequentially, the acquisition function 153 sequentially specifies display periods that are changed sequentially and the calculation function 154 calculates a statistic for each display period. For example, a case where a kurtosis is calculated for each display period will be described below.

As illustrated in FIG. 15, the display control function 152 displays a history of calculated kurtoses. In other words, the display control function 152 gives the display while updating the graph each time a kurtosis is calculated and scrolling the entire graph leftward such that the right end of a display area corresponds to the current time. The display control function 152 may display the graph represented in FIG. 5 together with display of vital data in time series by a line chart, a box plot chart, or the like, or a histogram.

When the kurtosis varies unstably on the history display in FIG. 15 while the operator is scrolling the display period sequentially, the operator is able to determine that the condition of the patient is not stable. When the kurtosis increases rapidly while the operator is scrolling the display period sequentially, the operator is able to determine that an abnormal value resulting from an error in measurement or input is contained in a new display area.

Figure 16:
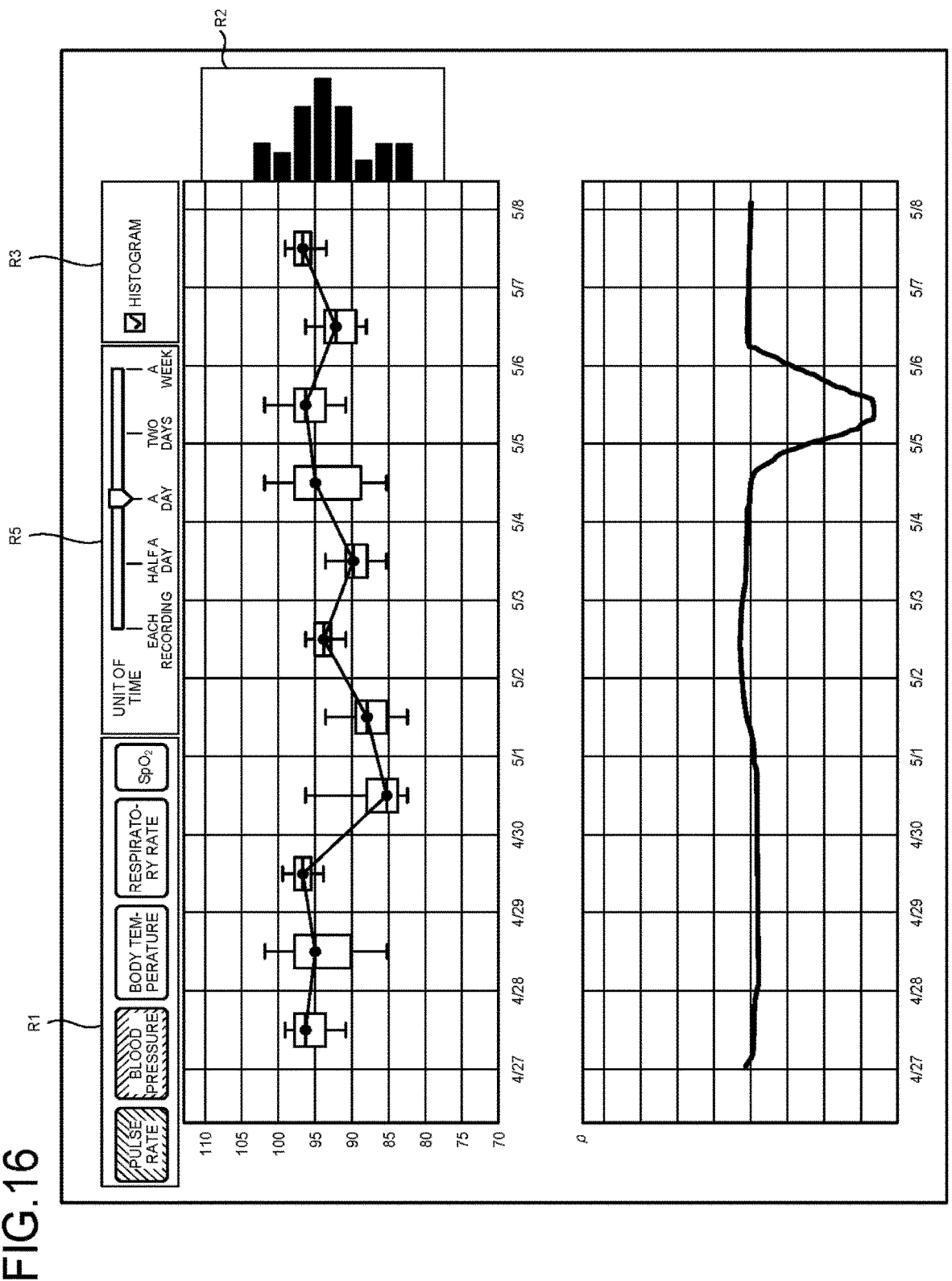
FIG. 16 is a diagram illustrating exemplary display of statistical information according to the third embodiment.

With reference to FIG. 16, other exemplary display of statistical information according to the third embodiment will be described. FIG. 16 is a diagram illustrating exemplary display of statistical information according to the third embodiment.

First of all, the calculation function 154 acquires multiple types of vital data. For example, the calculation function 154 accepts an operation to specify types of vital data from the operator via the input interface 130, thereby acquiring multiple types of vital data. In an example, the calculation function 154 accepts selecting buttons represented in the area R1 in FIG. 16, thereby acquiring multiple types of vital data. For example, when multiple types of vital data are displayed in time series, the calculation function 154 acquires the types of the vital data displayed in time series. A case where the calculation function 154 acquires "pulse rate" and "blood pressure" as multiple types of vital data will be described below.

The calculation function 154 calculates a value representing correlativity between "pulse rate" and "blood pressure". For example, the calculation function 154 calculates a correlation coefficient ρ between "pulse rate" and "blood pressure" contained in the display period or the specified period. For example, the calculation function 154 calculates a correlation coefficient ρ between "pulse rate" and "blood pressure" for each of segments of time obtained by segmenting the display period or the specified period at each unit of time.

The display control function 152 then displays the correlation coefficient ρ. For example, as illustrated in FIG. 16, the display control function 152 displays the correlation coefficients ρ that are calculated for the respective segments of time in a graph in association with the time axis. As illustrated in FIG. 16, the display control function 152 may display the graph representing the correlation coefficients ρ together with display of vital data in time series by a line chart, a box plot chart, or the like, and a histogram.

The first to third embodiments have been described. In addition to the above-described embodiments, various different modes may be carried out.

The above-described embodiments illustrate vital data; however, embodiments are not limited thereto and various types of numerical data representing medical information may be used.

For example, the above-described embodiments may be applied, not only to vital data, but also to various types of numerical data representing information about examination on the patient. Exemplary numerical data representing information about examination on the patient includes, in addition to vital data, data about examination on a specimen (such as blood), measurement data of images that are acquired from the patient (such as blood vessel diameter and blood flow), dietary intake of the patient (such as total calorie intake and ratio of leftovers to served food) and the number of steps per day.

For example, the medical information processing system 1 includes a specimen examination server that files data about examination on a specimen instead of the electronic medical record storage apparatus 300 or in addition to the electronic medical record storage apparatus 300. In this case, the I/F circuitry 110 receives the examination data from the specimen examination server and outputs the received examination data to the processing circuitry 150.

For example, the medical information processing system 1 further includes a picture archiving communication system (PACS) server instead of the electronic medical record storage apparatus 300 or in addition to the electronic medical record storage apparatus 300. In this case, the I/F circuitry 110 receives image measurement data from the PACS server and outputs the received measurement data to the processing circuitry 150.

The case where the electronic medical record storage apparatus 300, the specimen examination server and the PACS server store numerical data has been described. Alternatively, the memory 120 may store numerical data. For example, the memory 120 may store vital data, data about examination on a specimen, image measurement data, etc., in association with time. In an example, first of all, the I/F circuitry 110 receives image data from the PACS server and outputs the received image data to the processing circuitry 150. The processing circuitry 150 then calculates measurement data, such as a blood vessel diameter and a blood flow, from the image data and stores the calculated measurement data in the memory 120 in association with time at which the image data is acquired.

Figure 17:
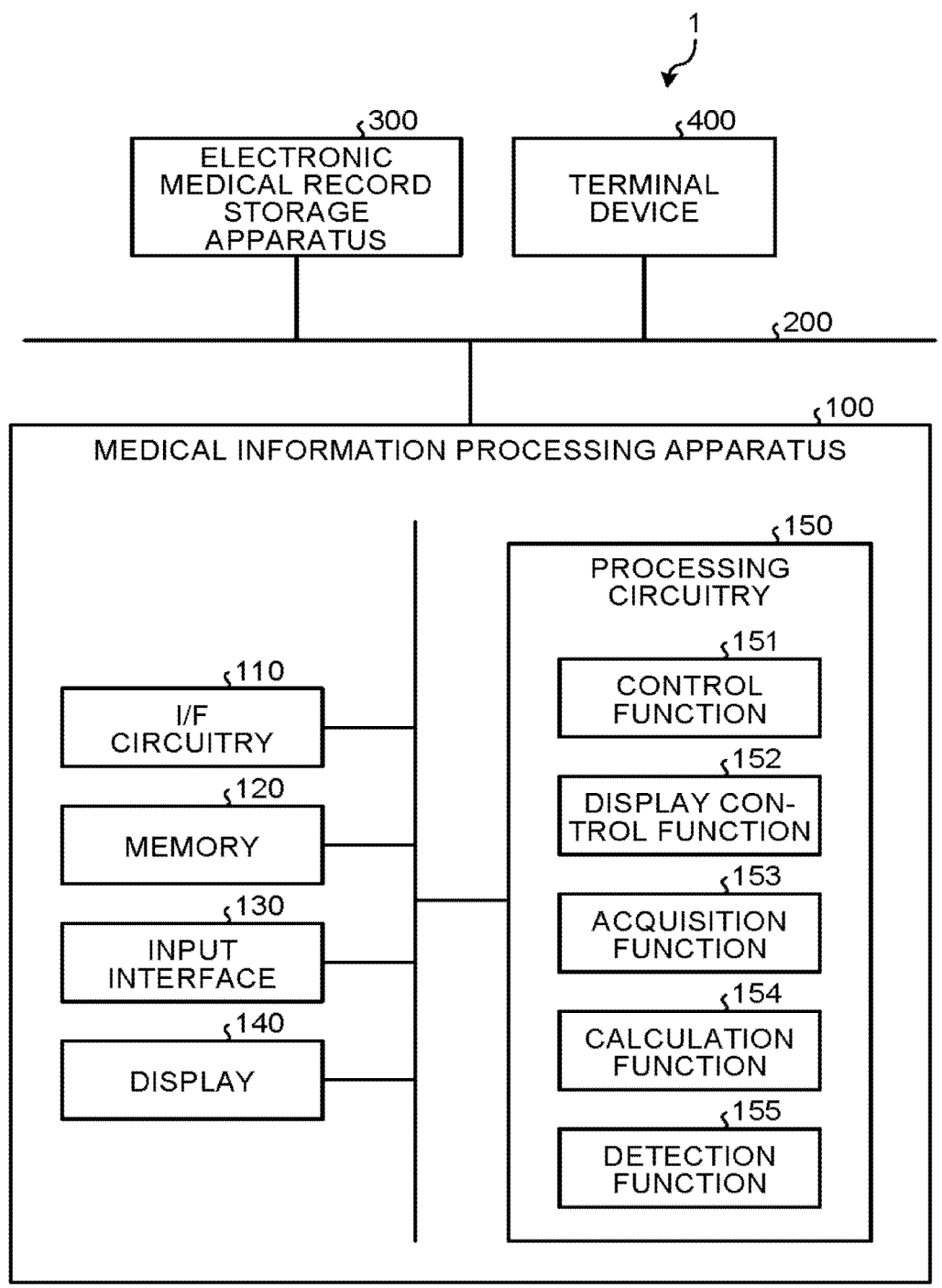
FIG. 17 is a block diagram illustrating an exemplary configuration of a medical information processing system according to a fourth embodiment.

The exemplary configuration illustrated in FIG. 1 has been represented as the configuration of the medical information processing system 1; however, embodiments are not limited thereto. For example, as illustrated in FIG. 7, the medical information processing system 1 may include a terminal device 400 in addition to the medical information processing apparatus 100, the network 200 and the electronic medical record storage apparatus 300. FIG. 17 is a block diagram illustrating an exemplary configuration of the medical information processing system 1 according to a fourth embodiment. As illustrated in FIG. 17, the medical information processing apparatus 100, the electronic medical record storage apparatus 300 and the terminal device 400 are connected with one another via the network 200 such that they can communicate with one another. The terminal device 400 is, for example, a tablet or a personal computer.

The terminal device 400 includes an input circuit 410 and a display 420 that are not illustrated in FIG. 17. The input circuit 410 converts an input operation that is accepted from an operator into electronic signals and output the electronic signals to the medical information processing apparatus 100. For example, the input circuit 410 is realized by a trackball, a switch button, a mouse, a keyboard, a touch panel, or the like.

The display 420 displays various types of data that is output from the medical information processing apparatus 100. For example, the display 420 is realized by a liquid crystal monitor, a cathode ray tube (CRT) monitor, a touch panel, or the like. The input circuit 410 and the display 420 may be integrated. For example, the input circuit 410 and the display 420 are realized by a touch panel.

For example, the display control function 152 accepts an instruction to display numerical data in time series from the operator via the input circuit 410 and displays numerical data representing medical information in time series. The acquisition function 153 specifies a display period and a specified period and the calculation function 154 calculates statistical information from the numerical data contained in the display period and the specified period. The display control function 152 causes the display 420 to display the statistical information. For example, the display control function 152 graphically displays a distribution of the numerical data contained in the display period or the specified period by a histogram, a box plot chart, etc. When the medical information processing system 1 includes the terminal device 400, the medical information processing apparatus 100 need not include the input interface 130 and the display 140. The medical information processing device 1 may include multiple terminal devices 400.

According to the configuration illustrated in FIG. 17, it is possible to represent the statistical information that is generated dynamically to the operator using the input circuit 410 and the display 420. In other words, if the operator has a tablet, a personal computer, or the like, the operator is able to refer to the statistical information that is calculated dynamically even in a room different from that where the medical information processing device 1 is set or a different hospital and thus understand data tendency easily.

The above-described embodiment illustrates the case where the statistical information about the vital data of the patient P1 is calculated; however, embodiments are not limited thereto. For example, the display control function 152 displays numerical data about multiple patients (for example, the patient P1, the patient P2 and a patient P3) in time series and the calculation function 154 calculates statistical information from the numerical data contained in the display period. The display control function 152 then displays the statistical information about the numerical data on the patients P1, P2 and P3 by a histogram, a box plot chart, etc.

For example, when the patients P1, P2 and P3 have the same case, the medical information processing system 1 is able to make it easy to understand data tendency corresponding to the case. When the same type of drug is administered to the patients P1, P2 and P3, the medical information processing system 1 is able to make it easy to understand data tendency corresponding to the type of drug to administer.

The above-described embodiment illustrates the case where each of the above-described processing functions is implemented by the processing circuitry 150; however, embodiments are not limited thereto. For example, the processing circuitry 150 may be configured by combining multiple independent processors and each processor may execute each program to implement each processing function. Each processing function of the processing circuitry 150 may be implemented in a way that each processing function is distributed to or integrated into a single or multiple processing circuits as appropriate.

The word "processor" used in the descriptions above refers to, for example, a central processing unit (CPU), a graphics processing unit (GPU) or a circuit, such as an application specific integrated circuit (ASIC) or a programmable logic device (for example, a simple programmable logic device (SPLD), a complex programmable logic device (CPLD) or a field programmable gate array (FPGA)). The processor implements the functions by reading and executing a program that is saved in the memory 120. Instead of saving the program in the memory 120, the program may be directly incorporated in the circuit of the processor. In this case, the processor reads the program that is incorporated in the circuit and executes the program to implement the functions. Each of the processors of the embodiment is not limited to the case where each processor is configured as a single circuit, and multiple independent circuits may be combined into a single processor to implement the functions.

The program that is executed by the processor is incorporated in a read only memory (ROM), a storage circuit, or the like, in advance and provided. The program may be recorded in a file in a format installable in these devices or executable by these devices in a computer-readable recording medium, such as a compact disk (CD)-ROM, a flexible disk (FD), a CD-R (recordable) or a digital versatile disk (DVD). The program may be stored in a computer that is connected to a network, such as the Internet, and may be downloaded via the network and thus provided or distributed. For example, the program may consist of modules containing each of the above-described functions. In practical hardware, the CPU reads the program from the storage medium, such as a ROM, and executes the program and accordingly each module is loaded into a main storage device and generated in the main storage device.

Each of the components of each of the devices according to the above-described embodiments is a functional idea and thus need not necessarily be configured physically as unillustrated in the drawings. In other words, specific modes of distribution and integration of the devices are not limited to those illustrated in the drawings, and all or part of the devices may be configured in a distributed or integrated manner functionally or physically in any unit according to various types of loads and the situation in which the devices are used. Furthermore, all or any part of the processing functions performed by the devices may be implemented by a CPU and a program that is analyzed and executed by the CPU or may be implemented as hardware based on a wired logic.

Furthermore, it is possible to implement the processing method in the above-described embodiment by executing a program, which is prepared in advance, with a computer, such as a personal computer or a work station. The control program may be distributed via a network, such as the Internet. The image processing program may be recorded in a computer-readable recording medium, such as a hard disk, a flexible disk (FD), a CD-ROM, a MO or a DVD, and may be read by the computer from the recording medium and thus executed.

According to at least one of the above-described embodiments, it is possible to make it easy to understand tendency of data that is acquired in time series from a patient, such as vital data.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical information processing system comprising processing circuitry configured to
   acquire numerical data representing medical information together with date and time information associated with the numerical data,
   display a first graph having a time axis based on the date and time information and an axis representing the numerical data,
   specify a period relating to the numerical data displayed in the first graph,
   calculate a distribution of the numerical data contained in the period, and
   further display the distribution graphically, wherein the processing circuitry is configured to display the first graph and a second graph having an axis representing the numerical data and an axis representing the distribution such that the axis representing the numerical data is shared between the first graph and the second graph, wherein
   the time axis of the first graph has a first end and a second end,
   the axis representing the numerical data of the first graph is located at the first end, and
   the axis representing the numerical data of the second graph is located at the second end.

2. The medical information processing system according to claim 1, wherein the processing circuitry is configured to specify, as the period, a display period for the numerical data displayed in time series.

3. The medical information processing system according to claim 2, wherein the processing circuitry is configured to detect an operation to change the display period and specify the changed display period as the period.

4. The medical information processing system according to claim 1, wherein the processing circuitry is configured to
   detect an operation to specify a specified period in a display period for the numerical data displayed in time series, and
   specify the specified period as the period.

5. The medical information processing system according to claim 1, wherein the processing circuitry is configured to
   specify multiple periods each of which is the period,
   calculate the distribution for each of the multiple periods, and
   display the distribution graphically for each of the multiple periods.

6. The medical information processing system according to claim 1, wherein the processing circuitry is configured to display a histogram as the distribution.

7. The medical information processing system according to claim 5, wherein the processing circuitry is configured to display, as the distributions, histograms that are generated for the multiple periods respectively.

8. The medical information processing system according to claim 7, wherein the processing circuitry is configured to superimpose and display the histograms, which are generated for the multiple periods respectively.

9. The medical information processing system according to claim 8, wherein the processing circuitry is configured to superimpose and display the histograms, which are generated for the multiple periods respectively, such that the longer an elapsed time after the generation of a displayed histogram, the greater a transparency of the displayed histogram.

10. The medical information processing system according to claim 7, wherein the processing circuitry is configured to display the histograms, which are generated for the multiple periods respectively, side by side.

11. The medical information processing system according to claim 7, wherein the processing circuitry is configured to display a difference between the histograms that are generated for the multiple periods respectively.

12. The medical information processing system according to claim 1, wherein the processing circuitry is configured to calculate the distribution for each of segments of time obtained by segmenting the period at each unit of time and graphically display the distributions each for each of the segments of time in time series.

13. The medical information processing system according to claim 12, wherein the processing circuitry is configured to calculate the unit of time according to a display period for the numerical data displayed in time series and calculate the distribution for each of the segments of time obtained by segmenting the period at each unit of time.

14. The medical information processing system according to claim 1, wherein the processing circuitry is configured to acquire the numerical data in multiple types,
 further calculate, for the numerical data contained in the period, a value representing correlativity between the numerical data in different types chosen from a pulse rate, a blood pressure, a body temperature, a respiratory rate and SpO2, and
 further display the value representing the correlativity.

15. The medical information processing system according to claim 1, wherein the processing circuitry is configured to, each time the processing circuitry acquires the period, calculate a statistic of the numerical data, and
 further display a history of the calculated statistics.

16. The medical information processing system according to claim 1, wherein the processing circuitry is configured to further display a result of comparison between the numerical data contained in the period and thresholds.

17. The medical information processing system according to claim 1, wherein the processing circuitry is configured to further calculate thresholds based on the numerical data contained in the period, and
 further display a result of comparison between the numerical data contained in the period and the thresholds.

18. The medical information processing system according to claim 1, wherein the numerical data is numerical data representing information about examination on a patient.

19. The medical information processing system according to claim 1,
 wherein the axis representing the numerical data in the first graph and the axis representing the numerical data in the second graph are identical with respect to a type of numerical data and a scale of numerical data.

20. The medical information processing system according to claim 1, wherein the processing circuitry is configured to calculate the distribution using all of the numerical displayed in the graph.

* * * * *